United States Patent
Plaxco et al.

(10) Patent No.: US 11,946,098 B2
(45) Date of Patent: Apr. 2, 2024

(54) CALIBRATION-FREE MEASUREMENT WITH ELECTROCHEMICAL BIOSENSORS

(71) Applicant: The Regents of the University of California, Oakland, CA (US)

(72) Inventors: Kevin Plaxco, Santa Barbara, CA (US); Hui Li, Wuhan (CN); Philip Dauphin-Ducharme, Santa Barbara, CA (US); Gabriel Ortega, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 615 days.

(21) Appl. No.: 16/618,352

(22) PCT Filed: Jun. 1, 2018

(86) PCT No.: PCT/US2018/035648
§ 371 (c)(1),
(2) Date: Nov. 30, 2019

(87) PCT Pub. No.: WO2018/223024
PCT Pub. Date: Dec. 6, 2018

(65) Prior Publication Data
US 2020/0182820 A1 Jun. 11, 2020

Related U.S. Application Data

(60) Provisional application No. 62/513,796, filed on Jun. 1, 2017.

(51) Int. Cl.
*G01N 27/327* (2006.01)
*A61B 5/00* (2006.01)
*C12Q 1/6825* (2018.01)

(52) U.S. Cl.
CPC .......... *C12Q 1/6825* (2013.01); *A61B 5/6867* (2013.01)

(58) Field of Classification Search
CPC ........... G01N 27/3275; G01N 27/3277; G01N 27/3274; C12Q 2565/519;
(Continued)

(56) References Cited

U.S. PATENT DOCUMENTS

| 8,003,374 B2 | 8/2011 | Heeger et al. |
| 2003/0022150 A1 | 1/2003 | Sampson et al. |

(Continued)

FOREIGN PATENT DOCUMENTS

| WO | 2016190727 A1 | 12/2016 |
| WO | 2018223024 A2 | 12/2018 |
| WO | 2018223024 A3 | 3/2019 |

OTHER PUBLICATIONS

International Search Report (from a corresponding foreign application), PCT/US18/35648, dated Jan. 21, 2019.
(Continued)

*Primary Examiner* — Gurpreet Kaur

(57) ABSTRACT

Electrochemical sensors have great promise for point-of-care and in vivo measurement of medically relevant molecules. However, the need for calibrating individual sensors limits the practical applicability of these sensing platforms. The invention provides a novel method of operating electrochemical sensors which obviates the need to calibrate individual sensors against a sample of known concentration. The invention exploits the frequency dependence of electrochemical output signals and the dependence of output signals on the inherent electron transfer kinetics of a selected sensor design. By use of signals generated at a nonresponsive frequency, a normalizing output value is generated that accounts for sensor-to-sensor variation and which enables an accurate calculation of target concentration. The scope of the
(Continued)

invention also includes pre-calibrated sensors that may be utilized without calibration steps.

11 Claims, 11 Drawing Sheets

(58) Field of Classification Search
CPC ............ C12Q 2565/607; C12Q 1/6816; C12Q 1/6825; A61B 5/6867
See application file for complete search history.

(56) References Cited

U.S. PATENT DOCUMENTS

| | | | |
|---|---|---|---|
| 2005/0112605 | A1 | 5/2005 | Heeger et al. |
| 2007/0154909 | A1 | 7/2007 | Xiao et al. |
| 2011/0210017 | A1* | 9/2011 | Lai ..................... G01N 33/5438 205/792 |
| 2014/0102915 | A1 | 4/2014 | Hu et al. |
| 2016/0166186 | A1* | 6/2016 | Ferguson ............. A61B 5/1473 600/366 |
| 2016/0190727 | A1 | 6/2016 | Kataoka et al. |

OTHER PUBLICATIONS

International Preliminary Report on Patentability for International Application PCT/US2018/035648, Report dated Dec. 3, 2019, dated Dec. 12, 2019, 11 Pgs.
International Search Report and Written Opinion for International Application No. PCT/US2018/035648, Search completed Jan. 21, 2019, dated Jan. 21, 2019, 14 Pgs.
Arroyo-Currás et al., "Real-time measurement of small molecules directly in awake, ambulatory animals", PNAS, vol. 114, No. 4, Jan. 24, 2017, pp. 645-650.
Baker et al., "An Electronic, Aptamer-Based Small-Molecule Sensor for the Rapid, Label-Free Detection of Cocaine in Adulterated Samples and Biological Fluids", Journal of the American Chemical Society, vol. 128, No. 10, Feb. 18, 2006, pp. 3138-3139.
Bonham et al., "Detection of IP-10 protein marker in undiluted blood serum via an electrochemical E-DNA scaffold sensor", Analyst, vol. 138, No. 19, Jul. 2013, pp. 5580-5583.
Boon et al., "Mutation detection by electrocatalysis at DNA-modified electrodes", Nature Biotechnology, vol. 18, Oct. 2000, pp. 1096-1100.
Cash et al., "An Electrochemical Sensor for the Detection of Protein-Small Molecule Interactions Directly in Serum and Other Complex Matrices", Journal of the American Chemical Society, vol. 131, No. 20, May 4, 2009, pp. 6955-6957.
Dauphin-Ducharme et al., "Maximizing the Signal Gain of Electrochemical-DNA Sensors", Analytical Chemistry, vol. 88, No. 23, Nov. 2, 2016, pp. 11654-11662.
Demchenko, "The problem of self-calibration of fluorescence signal in microscale sensor systems", Lab on a Chip, vol. 5, No. 11, Sep. 27, 2005, pp. 1210-1223.
Feld et al., "Trinuclear Ruthenium Clusters as Bivalent Electrochemical Probes for Ligand-Receptor Binding Interactions", Langmuir, vol. 28, No. 1, Nov. 4, 2011, pp. 939-949.
Ferapontova et al., "An RNA Aptamer-Based Electrochemical Biosensor for Detection of Theophylline in Serum", Journal of the American Chemical Society, vol. 130, No. 13, Mar. 7, 2008, pp. 4256-4258.

Ferguson et al., "Real-Time, Aptamer-Based Tracking of Circulating Therapeutic Agents in Living Animals", Sci. Transl. Med., 2013, vol. 5, Issue 213, pp. 1-10, XP055687148, DOI: 10.1126/scitranslmed.3007095.
Heller et al., "Electrochemical Glucose Sensors and Their Applications in Diabetes Management", Chemical Reviews, vol. 108, No. 7, May 9, 2008, pp. 2482-2505.
Kilo, Sr. et al., "Evaluation of a new blood glucose monitoring system with auto-calibration for home and hospital bedside use", Diabetes Research and Clinical Practice, vol. 74, No. 1, Oct. 2006, pp. 66-74.
Klonoff, "Point-of-Care Blood Glucose Meter Accuracy in the Hospital Setting", Diabetes Spectrum, vol. 27, No. 3, Aug. 2014, pp. 174-179.
Li et al., "A Biomimetic Phosphatidylcholine-Terminated Monolayer Greatly Improves the In Vivo Performance of Electrochemical Aptamer-Based Sensors", Angewandte Chemie International Edition, vol. 56, No. 26, Jun. 19, 2017, pp. 7492-7495.
Li et al., "Dual-reporter drift correction to enhance the performance of electrochemical aptamer-based sensors in whole blood", Journal of the American Chemical Society, Nov. 22, 2016, vol. 138, No. 49, pp. 15809-15812, XP055687145, ISSN: 0002-7863, DOI: 10.1021/jacs.6b08671.
Liu et al., "Micropatterned Aptasensors for Continuous Monitoring of Cytokine Release from Human Leukocytes", Analytical Chemistry, vol. 83, No. 21, Sep. 26, 2011, pp. 8286-8292.
Lubin et al., "Folding-Based Electrochemical Biosensors: The Case for Responsive Nucleic Acid Architectures", Accounts of Chemical Research, vol. 43, No. 4, Mar. 4, 2010, pp. 496-505.
Lubin et al., "Sequence-Specific, Electronic Detection of Oligonucleotides in Blood, Soil, and Foodstuffs with the Reagentless, Reusable E-DNA Sensor", Analytical Chemistry, vol. 78, No. 16, Jul. 13, 2006, pp. 5671-5677.
Noble et al., "Clinical Evaluation of a Novel On-Strip Calibration Method for Blood Glucose Measurement", Journal of Diabetes Science and Technology, vol. 8, No. 4, Jul. 2014, pp. 766-775.
Stojanovic et al., "Aptamer-Based Folding Fluorescent Sensor for Cocaine", Journal of the American Chemical Society, May 4, 2001, vol. 123, No. 21, pp. 4928-4931.
Swensen et al., "Continuous, Real-Time Monitoring of Cocaine in Undiluted Blood Serum via a Microfluidic, Electrochemical Aptamer-Based Sensor", J Am Chem Soc. Apr. 1, 2009; 131(12): 4262-4266.
White et al., "Exploiting Binding-Induced Changes in Probe Flexibility for the Optimization of Electrochemical Biosensors", Analytical Chemistry, vol. 82, No. 1, Dec. 10, 2009, pp. 73-76.
Xiao et al., "Electrochemical Detection of Parts-Per-Billion Lead via an Electrode-Bound DNAzyme Assembly", J. Am. Chem. Soc. 2007, 129, 2, 262-263.
Xiao et al., "Preparation of Electrode-Immobilized, Redox-Modified Oligonucleotides for Electrochemical DNA and Aptamer-Based Sensing", Nature Protocols, 2007, vol. 2, No. 11, pp. 2875-2880, XP055593151, DOI: 10.1038/nprot.2007.413.
Xiao et al., "Single-step electronic detection of femtomolar DNA by target-induced strand displacement in an electrode-bound duplex", PNAS, vol. 103, No. 45, Nov. 7, 2006, pp. 16677-16680.
Yue et al., "Real-Time Continuous Glucose Monitoring Shows High Accuracy within 6 Hours after Sensor Calibration: A Prospective Study", PLOS One, vol. 8, No. 3, Mar. 28, 2013, e60070, 6 pgs.
Zuo et al., "A Target-Responsive Electrochemical Aptamer Switch (TREAS) for Reagentless Detection of Nanomolar ATP", Journal of the American Chemical Society, vol. 129, No. 5, Jan. 18, 2007, pp. 1042-1043.

* cited by examiner

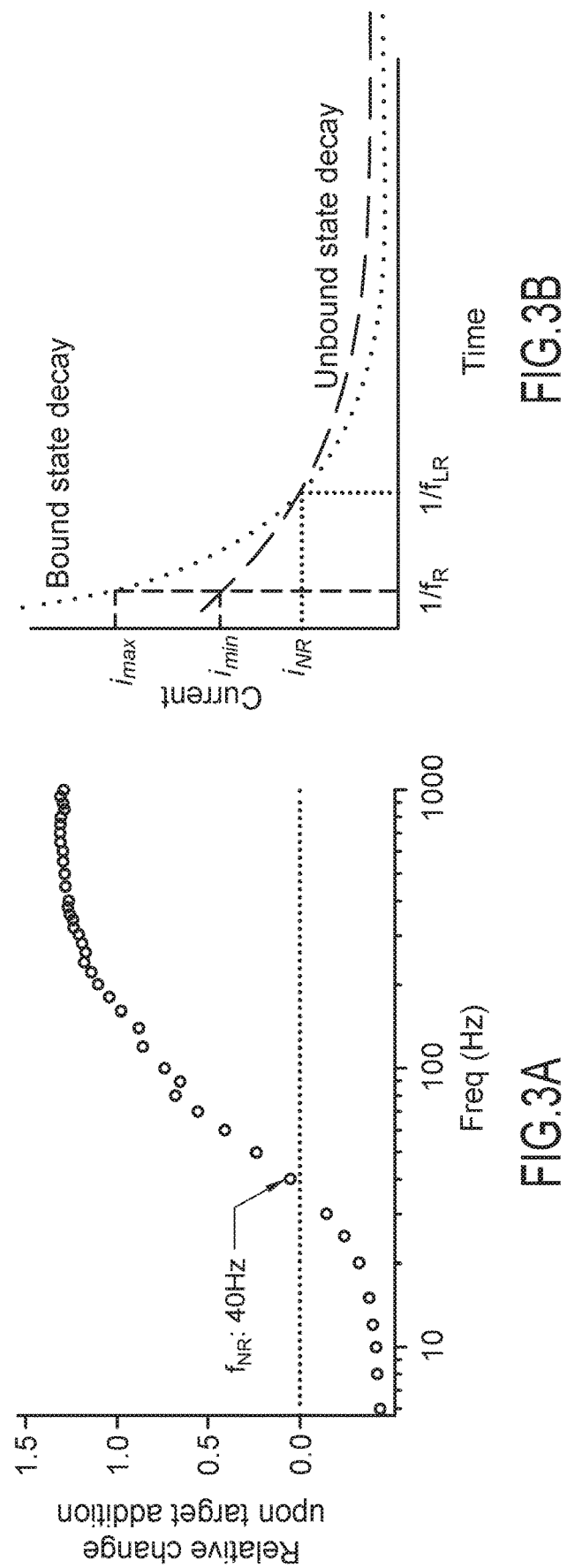

CALIBRATION-FREE MEASUREMENT WITH ELECTROCHEMICAL BIOSENSORS

CROSS-REFERENCE TO RELATED APPLICATIONS

This application claims priority to International Application No. PCT/US2018/035648, entitled "Calibration-free Electrochemical Biosensors," filed on Jun. 1, 2018, which claims priority to U.S. Provisional Application No. 62/513,796, entitled "Calibration-free Electrochemical Biosensors" filed on Jun. 1, 2017, each of which is incorporated by reference herein in its entirety.

BACKGROUND OF THE INVENTION

Improved methods for the measurement of diagnostically relevant molecules are needed to improve clinical outcomes and reduce healthcare costs. For example, the ability to quantify biomarkers in ex-vivo samples at the point of care is a critical substitute for laboratory testing in resource-limited regions, as these often lack the infrastructure necessary to maintain and utilize a network of centralized clinical facilities. Even in the relatively advantaged developed world, point-of-care tests augment centralized laboratory testing by speeding diagnosis, accelerating the initiation of treatment and reducing the need for follow-up visits, which in turn improves outcomes and lowers costs. To achieve practicality at the point of care, a technology must be simple (single-step, wash-free, reagent-free), rapid (for example, providing an answer within the 15 minutes of a typical provider/patient interaction), and low overhead (inexpensive, small).

E-AB sensors are able to measure their target directly even in complex clinical media, such as undiluted blood serum, without the need for reagent additions, washing, or any other processing steps. Critically, the equipment required for this measurement is easily miniaturized and brought directly to the point of care, even in resource-limited settings. Multiple groups, for example, have described construction of laptop- or smartphone-powered potentiostats supporting such sensors at a cost of less than US$100.

Exemplary E-AB systems include those described in Xiao, Y, Rowe, A. A., and Plaxco, K. W. (2007) Electrochemical detection of parts per billion lead via an electrode-bound DNAzyme assembly. *J Am. Chem. Soc.* 129, 262-263; U.S. Pat. No. 8,003,374 by Heeger, Fan, and Plaxco; Ferguson et al., "Real-time, aptamer-based tracking of circulating therapeutic agents in living animals," *Sci Transl Med.* 2013 Nov. 27; 5(213): 213ra165; and Swensen et al., "Continuous, Real-Time Monitoring of Cocaine in Undiluted Blood Serum via a Microfluidic, Electrochemical Aptamer-Based Sensor," *J Am Chem Soc.* 2009 Apr. 1; 131(12): 4262-4266.

Despite the great potential utility of E-AB sensors as a point-of-care molecular diagnostics, the platform still suffers from limitations that have hindered the practical deployment of this technology. First, while E-AB sensors are selective enough to work in undiluted blood serum, they tend to drift when deployed in undiluted whole blood, thus they have historically required the conversion of blood into serum prior to analysis. And although such conversion is relatively straightforward, it requires a degree of infrastructure ill-suited for use at the bedside or in the developing world. Second, the raw, absolute output signal produced by E-AB sensors varies significantly from sensor to sensor due to variations in fabrication. This variability is likely due to differences in the microscopic surface area of sensor electrodes and thus the total number and packing density of redox reporters that are exchanging electrons. Likewise, non-specific binding by non-target species present in the sample will often cause drift in sensor output.

In experimental or other controlled contexts, these problems can be circumvented by calibration using a target-free "blank," wherein the output current of the sensor is measured in a sample comprising zero target species. Using this blank current measurement, $i_0$, a relative signal gain, $(i-i_0)/i_0$, can be measured, which, in contrast to absolute sensor output current, is highly reproducible from sensor to sensor. Such calibration has proven sufficient for many applications, for example, continuous monitoring of an exogenously applied target or in benchtop applications wherein blank samples are readily available.

However, the critical calibration process cannot be applied in many settings, for example in the case of in vivo monitoring. Even for ex vivo applications, such as point-of-care applications, the need for calibration increases the complexity, time, and expense of the method and in many cases the calibration steps are beyond the practical capabilities of clinical or bedside applications. Thus, there is a need in the art for calibration-free measurement methods that can accurately quantify the concentration of a given molecular analyte irrespective of sensor-to-sensor variation or sensor drift.

SUMMARY OF THE INVENTION

The objective of the invention is to enable calibration-free measurement of a target analyte in a sample by an electrochemical sensor. The inventors of the present disclosure have advantageously developed a novel methodology for accurate measurement of analytes using electrochemical sensors wherein calibration against a standard is unnecessary. The methods of the invention are based upon the discovery that electrochemical sensors can be operated in a novel manner that provides a continuous normalization signal. To enable calibration-free measurement, the methods of the invention exploit the frequency dependency of electrochemical sensor signaling to generate a novel normalizing signal that can be used to correct for sensor-to-sensor variation without the need for separate calibration by a sample of known target concentration.

Thus, electrochemical sensors can be operated in a dual-frequency method. The first frequency comprises a normalization frequency, being a frequency that provides a sensor output (termed the "normalization signal") that is largely insensitive to analyte concentrations. The second frequency comprises a measurement frequency, being a frequency that provides a sensor output which is highly dependent upon the concentration of the target analyte in the sample. Both sensor outputs are subject to sensor-to-sensor variation (e.g. variability between sensors due to fabrication issues) and sensor drift, but the measurement output may be adjusted by the use of the normalization signal to provide an accurate assessment of target concentration irrespective of sensor-to-sensor variation or sensor drift.

The methods of the invention provide the art with calibration-free, rapid, single-step measurement of a target species in complex samples, live animals, and other contexts wherein a calibration step is impractical or impossible. The methods may be applied in complex samples such as whole, unprocessed blood using a convenient, real-time platform that is well suited for point-of-care applications as well as in vivo monitoring by implanted sensors. The methods of the invention may advantageously be employed using standard sensors and samples and do not require any specialized equipment or sample processing.

BRIEF DESCRIPTION OF THE DRAWINGS

FIG. 1A. E-AB sensors are comprised of an electrode-bound, redox reporter-modified recognition element, an aptamer in this depiction, that undergoes a binding-induced conformational change. The conformational change upon target binding alters the kinetics with which the reporter (here methylene blue, MB) exchanges electrons with the electrode, producing a target-dependent change in current when the sensor is interrogated via, for example, square wave voltammetry. FIG. 1B. Across a sweep of potential pulses at varying voltages, target binding induces a detectable change in sensor current output.

FIG. 2A. Due to sensor-to-sensor variations, the absolute currents output by individual E-AB sensors vary dramatically from sensor to sensor. FIG. 2A depicts target titrations of three independently hand-fabricated cocaine-detecting E-AB sensors interrogated in blood serum. While both the maximum and minimum currents observed ($i_{max}$ and $i_{min}$, respectively) vary significantly from sensor to sensor, the ratio $i_{max}/i_{min}$ (denoted as γ) is constant from sensor to sensor, as is $K_D$, the dissociation constant based on the affinity of the recognition element for the target. FIG. 2B. The relative output of E-AB sensors 1-3 ($i/i_{min}$) is quite reproducible from sensor to sensor. FIG. 2C. Using a calibration step to determine $i_{min}$ via a single measurement in target-free reference sample, and knowledge of the constants $K_D$ and γ, E-AB sensors achieve excellent accuracy and precision over a broad range of target concentrations, within ±10% of the actual (spiked) concentration over the range from 20 μM to 300 μM and ±20% over the range from 10 μM to 600 μM. The error bars shown in 2C and in the following figures represent the standard deviation of at least three sensors.

FIGS. 3A and 3B. FIG. 3A. E-AB signaling arises due to a binding-induced change in electron transfer kinetics, and thus the relative change in current observed upon the addition of saturating target is strongly dependent of the square-wave voltammetry frequency used to interrogate the sensor. Enough so that there is a frequency at which the sensor does not respond to target. FIG. 3B. When subjected to a potential pulse (such as in square wave voltammetry), a redox-reporter-modified recognition element will produce an exponentially decaying current, with the lifetime of the decay depending on whether or not the recognition element is bound to its target. These curves cross at a specific time point ($=1/f_{NR}$) at which the currents produced by the two states are identical. At this instance, the observed current is independent of the relative populations of the two states the recognition element is populating.

FIG. 4A. A titration of output current $i_{NR}$ performed at the non-responsive frequency (40 Hz, open circles) of a cocaine-detecting E-AB sensor illustrates the extent to which $i_{NR}$ is independent of target concentration and thus proportional to $i_{min}$ irrespective of the presence or absence of target. The current observed at a responsive frequency (500 Hz, dashed line), in contrast, is strongly concentration-dependent. FIG. 4B. The proportionality constant, α, which relates $i_{min}$ to $i_{NR}$, is quite reproducible from sensor to sensor for a given class of sensors, as shown here for the same three cocaine-detecting sensors employed in FIG. 2A.

FIG. 5A depicts frequency sweeps at a range of cocaine concentrations for a cocaine-detecting E-AB sensor in undiluted serum to identify an/NR of 40 Hz wherein no change in signal output is seen at any target concentration. FIG. 5B depicts frequency sweeps at a range of cocaine concentrations for a cocaine-detecting E-AB sensor in undiluted whole blood to identify an $f_{NR}$, also seen at 40 Hz.

FIG. 6A. The use of $i_{NR}$, output current measured at the nonresponsive frequency, to normalize E-AB sensor outputs produces excellent accuracy and precision in the measurement of cocaine by sensors interrogated in undiluted blood serum, wherein which sensor-estimated concentrations are accurate to within ±10% of the spiked concentration over the concentration range 20 μM to 800 μM, and ±20% over the range 8 μM to 800 μM. FIG. 6B, similar results are achieved by the methods of the invention for measurements in undiluted whole blood, where the estimated concentrations are within ±10% of the spiked concentrations over the range 60 μM to 1 mM and ±20% over the range 20 μM to 2 mM. The dashed lines in both FIG. 6A and FIG. 6B represent ±20% accuracy bands.

FIGS. 7A, 7B, and 7C are diagrams demonstrating target-induced changes in redox-reporter currents for electrochemical sensors of various designs. FIG. 7A depicts sensors based on binding-induced changes in redox-reporter reorganization energy, which in turn alters electron transfer kinetics. FIG. 7B depicts sensors based on binding-induced changes in through-DNA electron tunneling. FIG. 7C depicts sensors based on sterically-induced changes in the efficiency with which a redox reporter approaches the electrode surface.

FIG. 8A depicts the excitation decay curves of a sensor employing a kanamycin-binding aptamer as its recognition element, wherein two kanamycin molecules bind the aptamer at higher concentrations. Thus, the current decay kinetics will differ depending upon which of three binding states the recognition element is in: a first with the aptamer being unbound, a second with a single target molecule bound, and a third wherein two target molecules bind. FIG. 8B depicts the frequency response of a kanamycin binding aptamer-based sensor.

DETAILED DESCRIPTION OF THE INVENTION

Figure 1A:
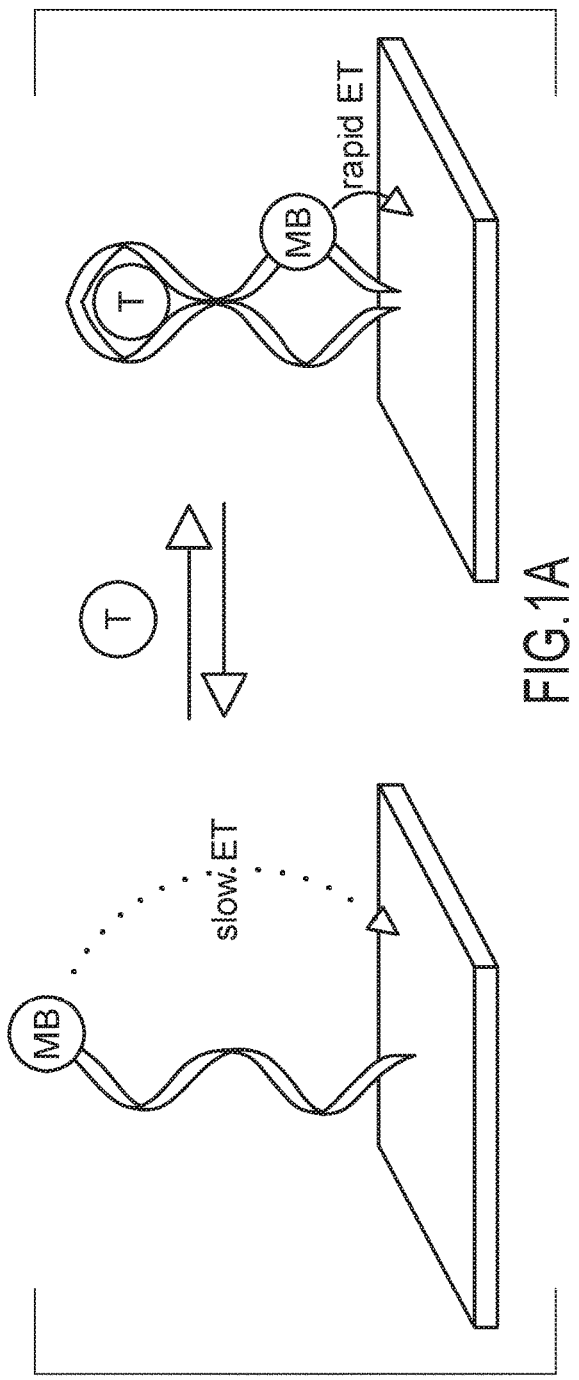
FIGS. 1A and 1B.
Figure 1B:
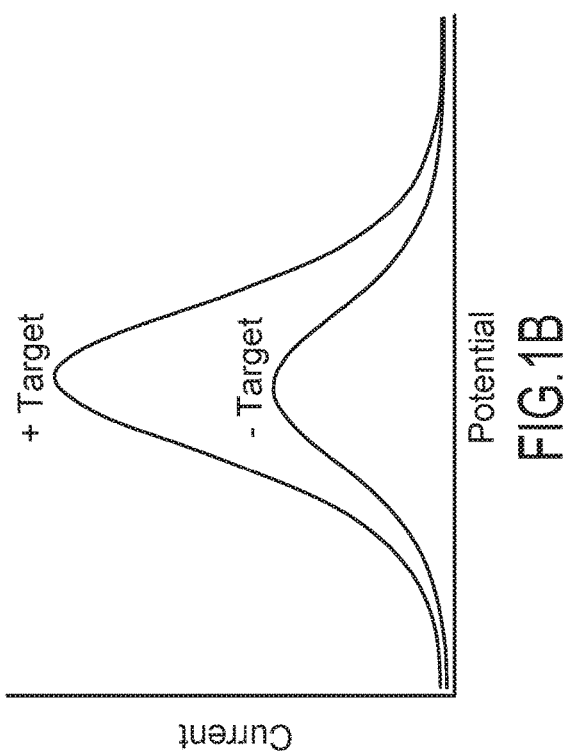

The various elements of the invention are described next.
Electrochemical Sensors.

The various embodiments of the invention are directed to electrochemical sensors and methods of operating such sensors. As used herein, an electrochemical sensor is any system of components:

comprising a plurality of recognition elements bound to an electrode substrate;

wherein each recognition element reversibly binds a target species;

wherein one or more redox reporter species is associated with each recognition element;

wherein the output of the sensor, upon application of a suitable potential pulse, is a current comprising electron flow between the redox reporter and the electrode substrate; and wherein the binding of the target species to the recognition elements alters the output current by changing the accessibility of the redox reporter to the electrode substrate, in a concentration-dependent manner.

It will be understood that the foregoing definition applies to variants of the enumerated system, for example, sensors having different types of outputs, e.g. voltages, alternative measures of electron transfer kinetics, and other types of electrical signals, wherein such electrical signals are based on or derived from currents comprising electron flow between the redox reporter and the electrode substrate.

Various sensor types may be utilized in the practice of the invention. In a first implementation, the sensor comprises an electrochemical aptamer-based sensor ("E-AB sensor"). Any E-AB sensor design or configuration known in the art may be used. In an E-AB sensor, the recognition element comprises an aptamer, as known in the art. The aptamer may comprise a DNA aptamer, RNA aptamer, or an aptamer comprising non-natural nucleic acids, as well as hybrids of the foregoing. It may also employ proteins or other macromolecules. While typical aptamers are about 15-60 bases in length, aptamers of any size may be used. Exemplary aptamers known in the art include those capable of binding target analytes such as doxorubicin, lysozyme, thrombin, HIV trans-acting responsive element, hemin, interferon, vascular endothelial growth factor, prostate specific antigen, dopamine, and cocaine.

In an E-AB sensor, one or more selected portions of the working electrode are functionalized with the aptamer. The aptamer may be conjugated to or otherwise associated with the electrode surface by any appropriate chemistry, for example by covalent bonding, chemisorption, or adsorption. For example, recognition elements may be thiolated for bonding to the electrode surface, using chemistries known in the art. The recognition element may be deposited on the electrode at any desired density, for example, at $0.1 \times 10^{11}$ to $1 \times 10^{13}$ molecules/cm$^2$. Additional steps to passivate exposed electrode surface are subsequently performed, as known in the art.

Each recognition element is functionalized with one or more redox species. Binding of the target species causes the recognition element to change its configuration, such that the position of (or the accessibility to the electrode of) the redox species is detectably altered. The redox species may comprise any composition of matter that interacts with the electrode such that a change in its accessibility to or proximity to the electrode causes a change in the electron transfer kinetics between it and the working electrode substrate, in response to application of an excitation potential pulse. Exemplary redox species include methylene blue, ferrocene, viologen, anthraquinone or any other quinones, ethidium bromide, daunomycin, organo-metallic redox labels, for example porphyrin complexes or crown ether cycles or linear ethers, ruthenium, bis-pyridine, tris-pyridine, bis-imidizole, cytochrome c, plastocyanin, ethylenetetracetic acid and cytochrome c'.

In one embodiment, the E-AB sensor is a dual-strand sensor, wherein the redox species is present on a separate strand, a portion of which is complementary to or otherwise capable of reversibly binding to a portion of the recognition element. In the presence of the target species, the redox reporter's strand is liberated from the recognition element, allowing the target species to bind to the recognition element and the redox reporter to come into contact with or proximity to the electrode. Exemplary dual-strand embodiments are described in Xiao et al. (2006) "Single-step electronic detection of femtomolar DNA by target-induced strand displacement in an electrode-bound duplex." *Proc. Natl. Acad. Sci. USA*, 103, 16677-16680.

The scope of the invention is not limited to E-AB sensors. The scope of the invention further encompasses any electrochemical sensor wherein binding-induced changes in a plurality of recognition elements on a working electrode create measurable changes in the electron transfer kinetics. For example, the recognition element may comprise any macromolecule undergoing a conformational change or other change that affects electron transfer between a redox reporter labeled recognition element and an electrode substrate upon target binding.

Recognition elements may comprise, for example, a nucleic acid sequence, peptide or protein, such as an antibody or a fragment thereof, or small molecules. Likewise, changes in redox reporter accessibility to the electrode may be induced by conformation change, steric hindrance when target species binds the recognition element, or other factors that induce changes in redox reporter-electrode current.

Figure 7A:
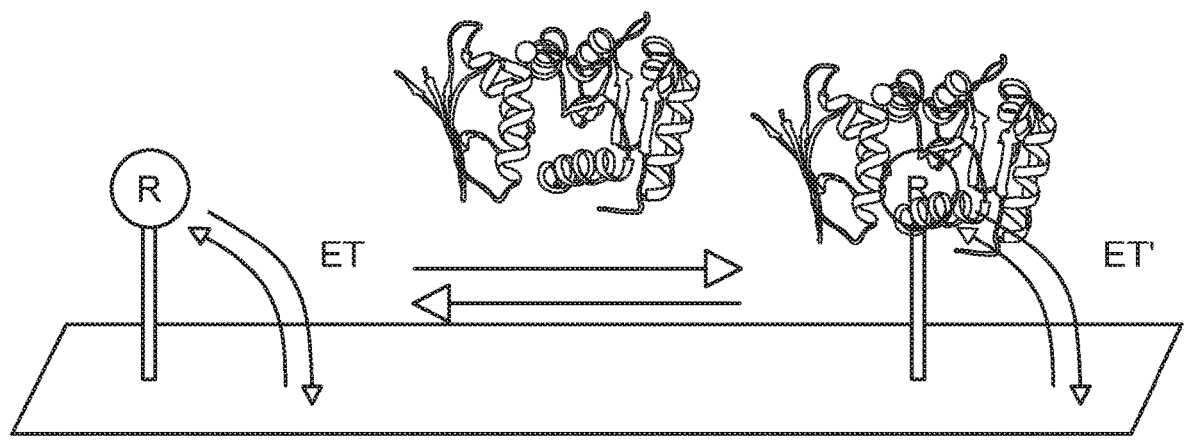
FIGS. 7A, 7B, and 7C.
Figure 7B:
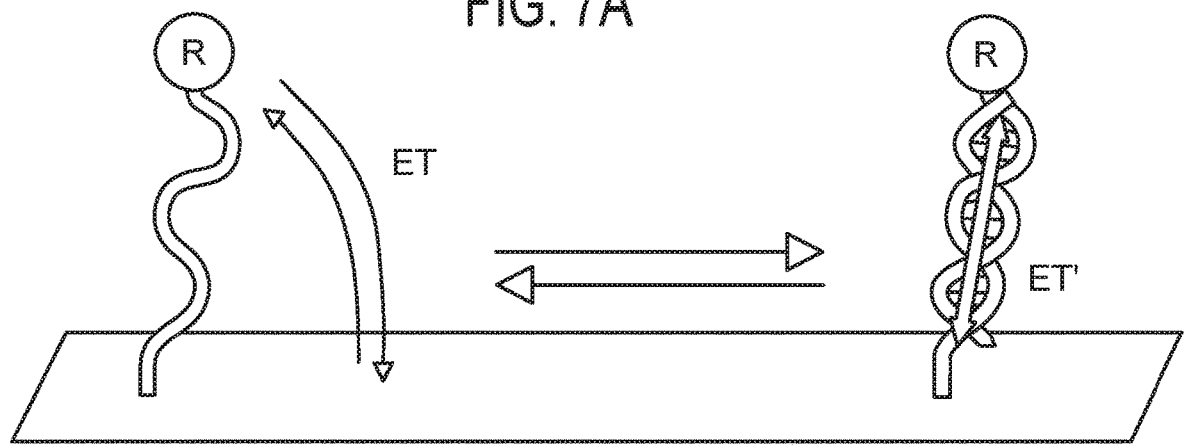
Figure 7C:
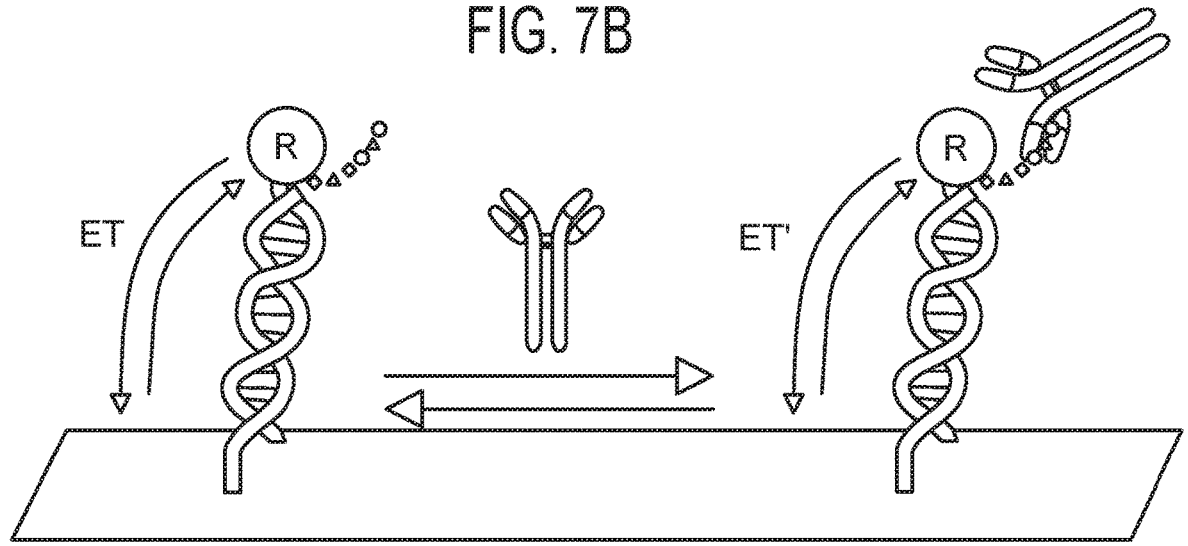

The electrochemical sensors of the invention may further encompass any electrochemical biosensor reliant on changes in electron transfer kinetics induced by binding of a target to a redox reporter-associated recognition element to generate an output signal. For example, the electrochemical sensor may comprise a sensor based on binding-induced changes in redox-reporter reorganization energy (and thus electron transfer kinetics), for example as described in Feld et al, "Trinuclear Ruthenium Clusters as Bivalent Electrochemical Probes for Ligand-Receptor Binding Interactions," *Langmuir*, 2012, 28 (1), pp 939-949. The electrochemical sensor may comprise a sensor based on binding-induced changes in through-DNA electron tunneling, for example as described in Boon et al., "Mutation detection by electrocatalysis at DNA-modified electrodes," Nat. Biotechnol. 2000, 18, 1096-1100. The electrochemical sensor may comprise a sensor based on sterically-induced or electrostatically-induced or hydrodynamically-induced changes in the efficiency with which a redox reporter approaches the electrode surface, for example as described in Cash et al., "An Electrochemical Sensor for the Detection of Protein—Small Molecule Interactions Directly in Serum and Other Complex Matrices," *J. Am. Chem. Soc.*, 2009, 131 (20), pp 6955-6957. Exemplary alternatives to E-AB sensors are depicted in FIGS. 7A, 7B, and 7C.

Sensor Components.

The electrochemical sensor will comprise one or more working electrodes. The working electrode may comprise any suitable electrode material for electrochemical sensing, including, for example: any metallic surface that forms a bond with thiols; gold; any gold-coated metal, (such as titanium, tungsten, platinum, carbon, aluminum, copper, etc); bare palladium electrodes.

The working electrode may be configured in any desired shape or size. For example, paddle-shaped electrodes, rectangular electrodes, electrode arrays, screen-printed electrodes, and other configurations may be used. For in vivo measurements, a thin wire configuration is advantageous, as the low-profile wire may be inserted into veins, arteries, tissue or organs and will not impede blood flow in blood vessels or cause substantial damage in tissues. For example, a wire having a diameter of 1-500 μm, for example, 100 μm, may be used. Exemplary wire E-AB configurations for in-vivo measurements are described, for example, in Arroyo-Currás et al., "Real-time measurement of small molecules directly in awake, ambulatory animals," *PNAS* 2017 114 (4) 645-650.

The electrochemical sensors of the invention may further comprise or be operated in combination with, a reference electrode, for example an Ag/AgCl electrode, or other reference electrode known in the art. The electrochemical sensors of the invention may further comprise or be operated in combination with an auxiliary or counter electrode, for example, a platinum auxiliary electrode. The electrochemical sensor of the invention may be configured in a three-electrode cell system. The three-electrode cell system may comprise one or more working, reference, and auxiliary electrodes, appropriately configured for performing voltammetry measurements. The three-electrode cell system may comprise a mixing chamber or other vessel wherein the electrodes are present and are contacted with the sample. The three-electrode cell system may comprise an implantable system for placement in the body of a living organism, such as a system configured in a wire conformation or housing.

The electrochemical sensors of the invention will be in functional connection with appropriate components for performing voltammetry or like measurements. The voltammetry components may comprise two or more devices in electrical and/or network connection with one another, or may comprise a single integrated device. Voltammetry components may include potientiostats or other voltage sources and voltage controllers. The system may further comprise appropriate circuitry for reading sensor outputs, and storing such outputs or routing the outputs to other devices. The systems of the invention may further comprise data processing means, for example, a general purpose computer or other data processor capable of carrying out the various calculations utilized in the methods of the invention. The scope of the invention further encompasses non-transitory computer-readable recording media having stored thereon an encoding program that causes a computer to execute a process, the process comprising one or more calculations set forth in the methods of the invention.

Target Species.

The various methods and sensors of the invention are directed to the measurement of one or more target species. The target species may be any inorganic or organic molecule, for example comprising a small molecule drug, a metabolite, a hormone, a peptide, a protein, a carbohydrate, a nucleic acid sequence, a pathogen, or any other composition of matter that can be selectively detected by an electrochemical sensor.

Exemplary target species include metabolites such as glucose, creatinine, hormones such as cortisol or A and B-type natriuretic peptides, and other biomarkers indicative of organ function, health, or disease status. Other target species may include drugs having significant side effects, such as chemotherapeutic drugs, and drugs having a narrow therapeutic index, wherein accurate measurement of blood levels would allow for safe dosing with minimal side effects.

Sample.

The target species of the invention are assessed in a sample. The sample may comprise any liquid or substantially aqueous composition. The sample may comprise whole blood, serum, plasma, interstitial fluid, cellular exudates, cellular extracts, foodstuffs, industrial aqueous samples, and environmental samples such as groundwater, or other complex liquids. In some embodiments, the sample is derived from a subject, for example a human patient or a non-human animal such as a veterinary subject or test animal. In one embodiment, the sample comprises blood (or serum derived therfrom) withdrawn from the subject in a blood draw or blood drop (e.g. finger stick). In one embodiment, the sample comprises aqueous samples in a living organism sampled by sensor elements implanted in the living organism. In one embodiment, the sample comprises flowing whole blood, by an implanted sensor element (e.g., in the circulatory system) of a subject. In one embodiment, the sample comprises interstitial fluid sampled by an implanted sensor in an organ or tissue of the subject. In an alternative embodiment, the sample is a gas.

The samples may be processed. Processing steps include concentration, dilution, filtration, centrifugation, and other common sample preparation steps known in the art. Advantageously, the methods of the invention enable sampling in complex, unprocessed samples and in one implementation, the sample is an unprocessed sample, for example, an undiluted sample, an unfiltered sample, or an unconcentrated sample.

Pulsed Voltammetry.

The sensors of the invention are utilized in a measurement protocol comprising a pulsed voltammetric method. A pulsed voltammetric method is an electrochemical measurement technique wherein the functionalized electrode of the sensor is subjected to a series of potentials applied in a pulsed waveform, and wherein one or more measurements of system current are assessed in each cycle.

In the practice of the invention, the series of potential pulses will comprise one or more suitable potential pulses, a suitable potential pulse being an applied potential at a value that generates a measurable current output from the redox reporter species utilized in the system. Generally, the series of potential pulses will comprise pulses at, near, or encompassing (i.e. in a sweep voltage method) the redox potential(s) of the one or more redox reporter species, i.e. being of a voltage capable of exciting and inducing a faradaic current flow between redox reporters of the sensor's recognition elements and the electrode.

In a first embodiment, the pulsed voltammetric method comprises square wave voltammetry (SWV), as known in the art. In SWV, a square voltage waveform is applied to the working electrode and faradic current in the cell is measured. The current may be sampled twice during each square wave cycle, once at the end of the forward pulse, and again at the end of the reverse pulse. The technique discriminates against charging current by delaying the current measurement to the end of the pulse. The difference in current between the two measurements is plotted against the applied potential. Square wave voltammetry yields peaks for faradaic processes, where the peak height is directly proportional to the concentration of the target species in solution. In SWV, the frequency of the waveform can be altered by changing the period of each applied pulse (and corresponding resting period).

The scope of the invention further encompasses other pulsed voltammetric techniques wherein a concentration-independent or concentration-insensitive signal is generated at a specific frequency or frequencies.

Frequency Dependent Sensor Output.

The scope of the invention encompasses methods of determining target species concentration in a sample using a novel dual-frequency methodology, as set forth below. The relationship between target concentration and the voltammetric signal (e.g., peak current), i, output by an electrochemical sensor is given by Equation 1:

$$[T] = K_D \frac{i - i_{min}}{i_{max} - i}. \qquad \text{Equation 1}$$

where [T] is the concentration of the target species, $K_D$ is the recognition element's dissociation constant, and $i_{min}$ and $i_{max}$ are the output signals that are observed in the absence of target ($i_{min}$) and in the presence of a level of target that effectively saturates the receptor ($i_{max}$).

The parameter $K_D$, the binding dissociation constant, as known in the art, is based on the inherent affinity of the recognition element for the target analyte. Therefore, $K_D$ is substantially constant for sensors of a given design, i.e. sensors utilizing a common type of recognition element and basic configuration, and being operated within a common range of measurements conditions, i.e., sensors of the same class.

The parameter γ is the ratio between $i_{max}$ to $i_{min}$, wherein $i_{max}$, is the output signal produced by a sensor in the presence of saturating abundance of target and $i_{min}$ is the output signal produced by the sensor in the absence of target. When measured at a responsive frequency, as described below, $i_{max}$ and $i_{min}$ are directly dependent upon the number of recognition elements on an individual sensor. The ratio of the two, γ, however, is independent of the number of recognition elements and instead is based on the inherent difference in electron transfer kinetics of the recognition element conjugated redox reporter when target is bound ($i_{max}$) vs. unbound ($i_{min}$). Accordingly, like $K_D$, γ is substantially constant for sensors of a given design, i.e. sensors utilizing a common type of recognition element and basic configuration, and being operated within a common range of measurements conditions, i.e., sensors of the same class.

With $K_D$ and γ being constant across individual sensors of a shared design, for sensors of that class, Equation 1 can be simplified to Equation 2:

$$[T] = K_D \frac{i - i_{min}}{\gamma i_{min} - i}. \quad \text{Equation 2}$$

The parameter, $i_{min}$, often varies dramatically from one sensor to the next due to significant sensor-to-sensor variation in the microscopic surface area of the sensing electrode and the density with which the receptors are packed onto it. This variation can be so great that, using conventional methods, without knowledge of the $i_{min}$ of each individual sensor, target concentrations cannot be derived from measurements of peak current, i.

However, the relative output signal change, the ratio of i to $i_{min}$, is well correlated with target concentration irrespective of any sensor-to-sensor variation in $i_{min}$. Thus, Equation 2 can be restated as Equation 3:

$$[T] = K_D \frac{\frac{i}{i_{min}} - 1}{\gamma - \frac{i}{i_{min}}}. \quad \text{Equation 3}$$

However, as determination of $i_{min}$ for an individual sensor is often not practical, a method is needed to estimate $i_{min}$ to avoid the need for individual sensor calibration. The inventors of the present disclosure have advantageously discovered a methodology for accurately and easily calculating $i_{min}$ values for sensors of a common class. The novel methods of the invention are based upon the strong frequency dependence of electrochemical sensing outputs.

The origins of the frequency response are as follows. When subjected to a potential pulse (such as in square wave voltammetry), a redox-reporter-modified recognition element will produce an exponentially decaying current, wherein the lifetime of the decay is dependent upon whether or not the recognition element is bound to its target. As depicted in FIG. 1A, target-bound recognition elements, in a signal-on type sensor, are in closer proximity to the electrode surface and thus the rate of electron transfer, in response to a potential pulse, is faster with a rapid decay constant (FIG. 3B). In contrast, unbound recognition elements, in response to a potential pulse have a slower decay, as depicted in FIG. 3B. These curves cross at a specific time point ($=1/f_{NR}$) at which the currents produced by the two states are identical. At this frequency, the observed current is independent of the relative populations of the two states the recognition element is populating. Square wave voltammetry can be made to sample the current at this specific time point by appropriately tuning its frequency. At the relevant frequency, $f_{NR}$, the output of the square wave voltammagram, $i_{NR}$, becomes independent of target concentration.

The inventors of the present disclosure have determined that there is a constant ratio, α, between the current observed at the non-responsive frequency, $i_{NR}$, and the current observed in a target-free sample, $i_0$. Like $K_D$ and γ this ratio is based on the inherent electron transfer kinetics of a particular sensor design and, under consistent operating conditions, will be constant and stable for all sensors having the same design. Advantageously, this previously unknown relationship enables the measurement of $i_{NR}$ to be used in the calculation of $i_{min}$.

Accordingly, $i_{min}$ can be derived easily from a measurement of the sample at the non-responsive frequency in addition to a measurement of i at a responsive frequency. Thus, target concentration may be estimated by means of Equation 4:

$$[T] = K_D \frac{i - \alpha i_{NR}}{\gamma \alpha i_{NR} - i} = K_D \frac{\frac{i}{i_{NR}} - \alpha}{\gamma \alpha - \frac{i}{i_{NR}}} \quad \text{Equation 4}$$

The relationship embodied in Equation 4 is based on the foregoing discoveries regarding α and γ and the invariance of these constants and that of $K_D$ for sensors of a selected design type, operated under common assay conditions. As used herein, a sensor of a selected design type means that the sensor is one of a plurality or class of sensors having sufficiently common design characteristics such that all sensors of the selected design type will respond similarly when utilized within a selected set of selected assay conditions. The sensor characteristics may comprise various factors, including: the configuration (e.g., size and shape) and material of the electrodes, sample chambers, and other sensor component parameters. The sensor characteristics may further encompass manufacturing methods, for example electrode cleaning and functionalization protocols. The sensor characteristics may further include the type of target species to be detected, the type of sample to be analyzed, the composition of the recognition element, the type of redox reporter(s), the packing density of the recognition elements on the working electrode, the electrode functionalization chemistry, the recognition element and redox reporter conjugation chemistry, and other sensor parameters that affect sensor output. Another common design parameter may be the sensor's manufacturing lot, wherein sensors in a class are those fabricated in the same allotment, using shared pools of component materials.

In one embodiment, a class of sensors comprises a plurality of sensors having identical sensor architecture, identical recognition elements and redox reporter elements, identical chemistries for attachment of the recognition elements to the working electrode, identical manufacturing methods, and similar recognition element packing densities (e.g., packing densities that vary by less than 10%, by less than 20%, or less than 30% among sensors within the batch).

Similarly, common assay conditions, as used herein, will refer to sensing operations performed on like sample types, with the samples prepared by like sample preparation techniques. Common assay conditions also means that assays are performed under like conditions, for example, using the same buffer compositions, and with substantially identical reaction parameters such as pH and osmolarity, for example, varying by less than 5%, less than 10%, less than 20%, etc., with assays performed at similar temperatures, for example varying by less than 1 degree, less than 2 degrees, or less than 5 degrees Celsius, etc.

Two designs and/or assay conditions will be considered common if measurement results achieved thereby in the methods of the invention are consistent within a desired degree of stringency. For example, two designs or assay conditions may be considered common if they achieve results that are not statistically different, or if the average results have reasonable variability, for example, varying by less than 30%, less than 25%, less than 20%, less than 15% less than 10%, less than 5%, etc.

Methods of the Invention.

The scope of the invention encompasses novel methods of measuring target concentration in a sample, enabled by the foregoing sensor phenomena derived by the inventors of the present disclosure. This calibration-free measurement technique can be advantageously be achieved by standard electrochemical sensors, with standard sample preparation and under standard assay conditions. In a general implementation, the scope of the invention comprises a method of measuring the concentration of a target species in a sample by the following process:

presenting the sample to an electrochemical sensor of a selected design, under a selected set of assay conditions; wherein the electrochemical sensor comprises a plurality of recognition elements bound to an electrode substrate; wherein each recognition element reversibly binds the target species at a known equilibrium dissociation constant value $K_D$ wherein one or more redox reporter species is associated with each recognition element; and wherein the output of the sensor, upon application of a suitable potential pulse, is a current comprising electron flow between the redox reporter and the electrode substrate;

performing a first interrogation comprising the application of a series of suitable potential pulses to the sensor at a responsive pulse frequency to obtain an output value i, wherein the responsive frequency is a frequency which results in a sensor output that is dependent upon the concentration of the target species in the sample;

performing a second interrogation of the sample comprising the application of a series of suitable potential pulses to the sensor at a nonresponsive pulse frequency to obtain an output value, $i_{NR}$, wherein the nonresponsive frequency is a frequency which results in a sensor output that is substantially independent of the concentration of the target species in the sample; and calculating the concentration of the target species, [T], by the equation $$[T] = K_D \frac{i - \alpha i_{NR}}{\gamma \alpha i_{NR} - i}$$

wherein $\gamma$ is a constant comprising the ratio of target-saturated output signal to target-free output signal for sensors of the selected design operated under the selected assay conditions;

wherein $\alpha$ is a constant comprising the ratio of $i_{NR}$ output signal to target-free output signal for sensors of the selected design operated under the selected assay conditions.

Figure 2A:
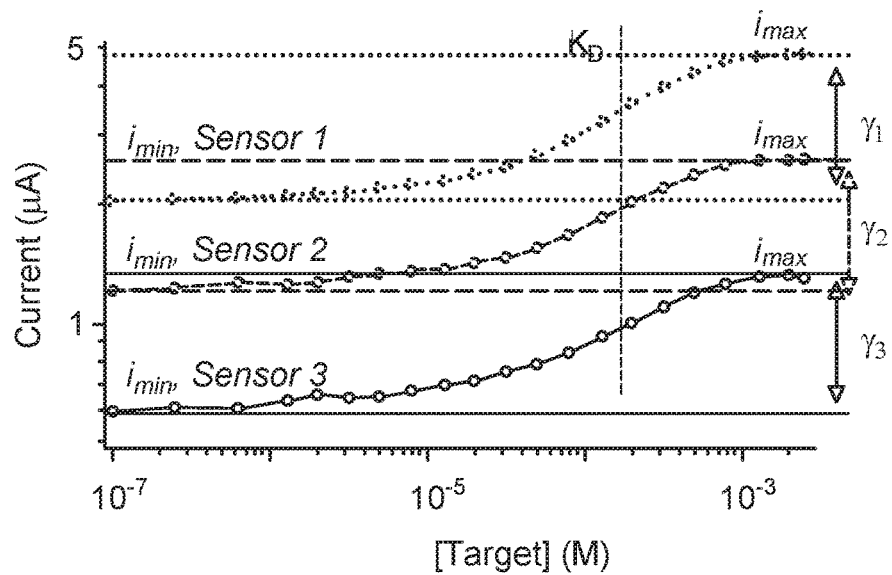
FIGS. 2A, 2B, and 2C.
Figure 2B:
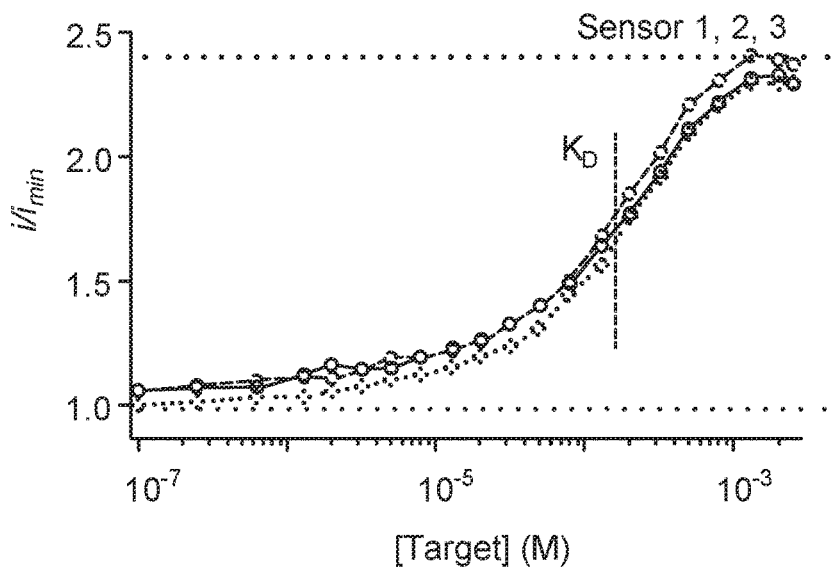
Figure 2C:
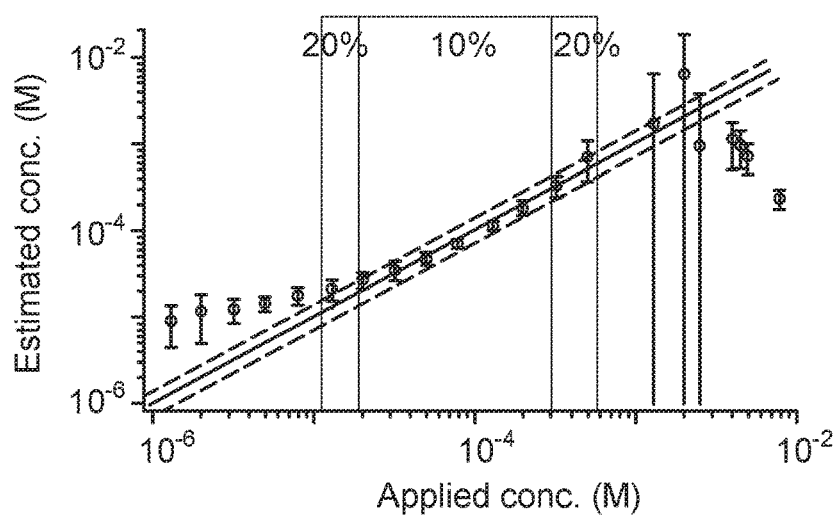
Figure 4A:
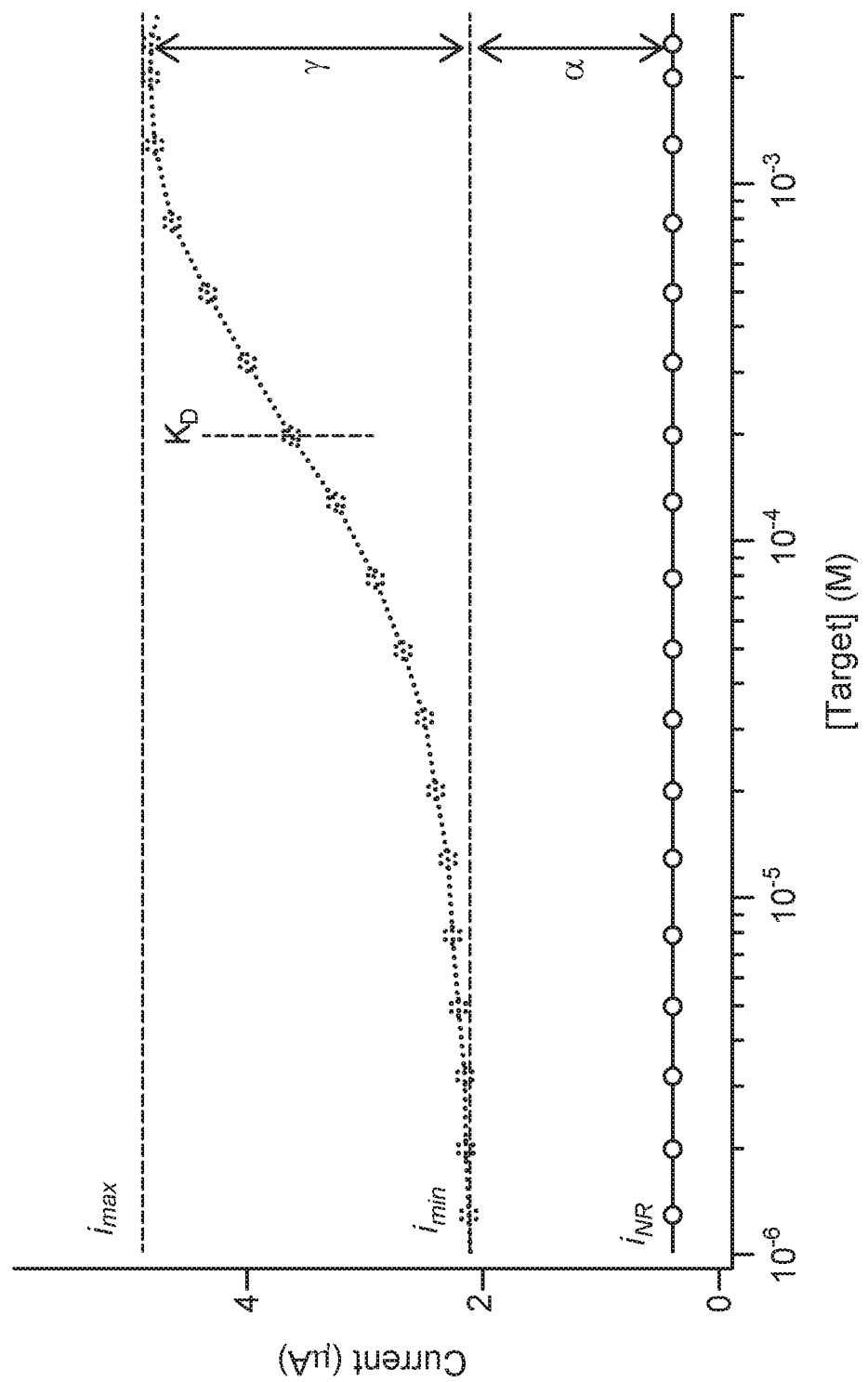
FIG. 4A and FIG. 4B.
Figure 4B:
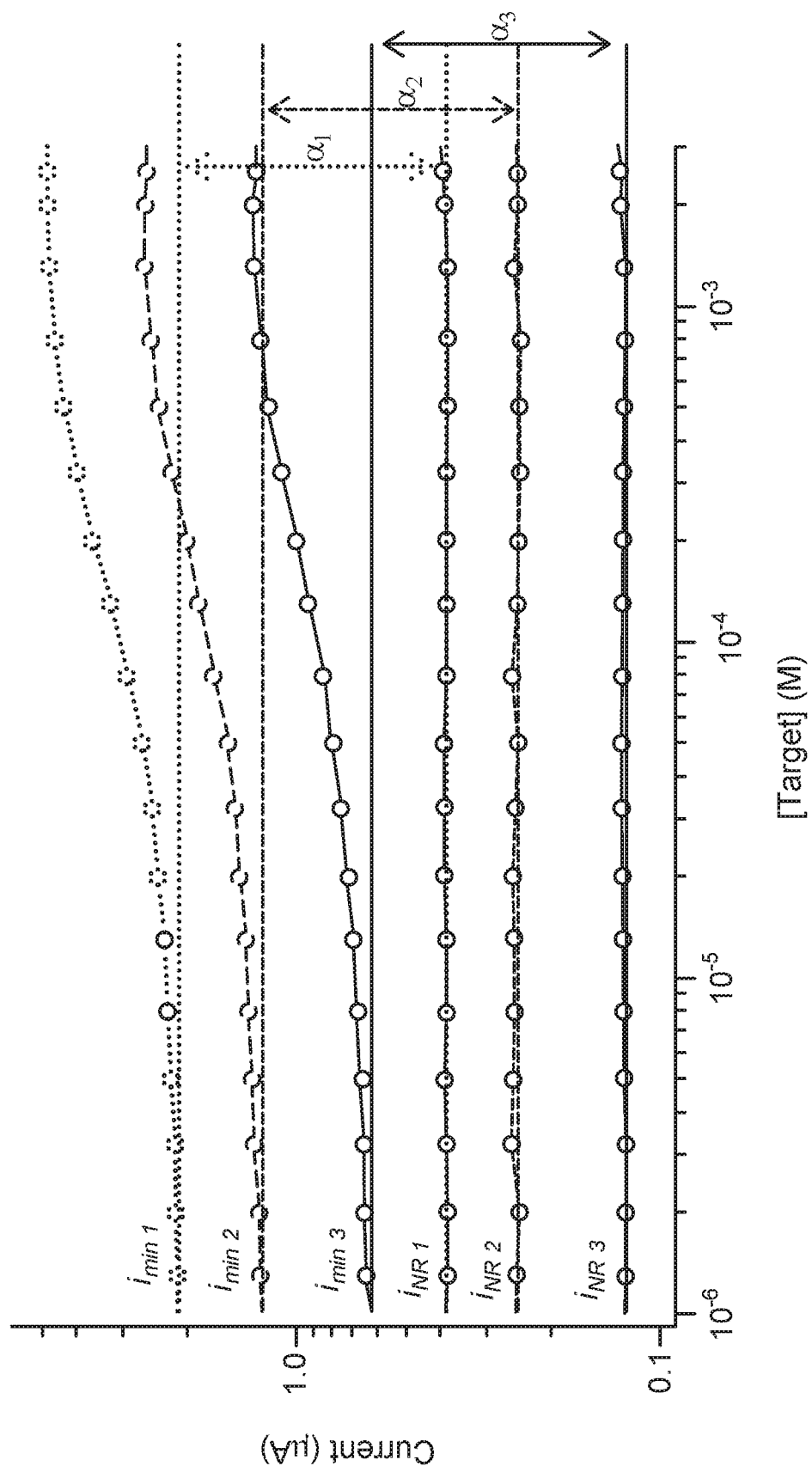

The non-responsive frequency, $f_{NR}$, and the constants utilized in the calculation of target concentration may be readily derived by the use of a training set comprising one or more sensors of the selected class, operated under the selected assay conditions. Depending on inherent variability of the sensors and assay conditions, and the desired degree of statistical stringency, the size of the training set may vary, for example from 1-100 sensors, for example, from three to ten sensors. As depicted in FIG. 2A and FIG. 4B, the parameters $F_{NR}$, $K_D$, $\alpha$, and $\gamma$ are, generally, remarkably stable across sensors and even with small training sets, accurate measurements may be attained for sensors of a given class.

The sensors of the training set may be tested at a range of frequencies to derive data for the determination of $f_{NR}$, the mean frequency at which the selected sensor design is insensitive to target concentration. Upon identification of $f_{NR}$ and selection of a responsive frequency, the output of the training set sensors may be titrated, at each frequency across a range of target concentrations, as in FIGS. 5A and 5B. Output current (i) vs. target concentration data may be utilized to calculate $K_D$, $\alpha$, and $\gamma$ to define these parameters for the class. In one embodiment, the output of the one or more sensors of a training set is tested across a range of frequencies (e.g., 1 to 10,000 Hz) to identify the nonresponsive frequency ($f_{NR}$) and responsive frequencies. A responsive frequency may be selected from the range of responsive frequencies, for example, a frequency having good signal to noise results. Following this derivation of $f_{NR}$ and selected of a responsive frequency, at both the nonresponsive frequency and the selected responsive frequency, sensor output is measured across a range of target concentrations and a global fitting, as known in the art, of Equation 4, or an equivalent combination of operations, is performed to derive $K_D$, $\alpha$, and $\gamma$.

Figure 5A:
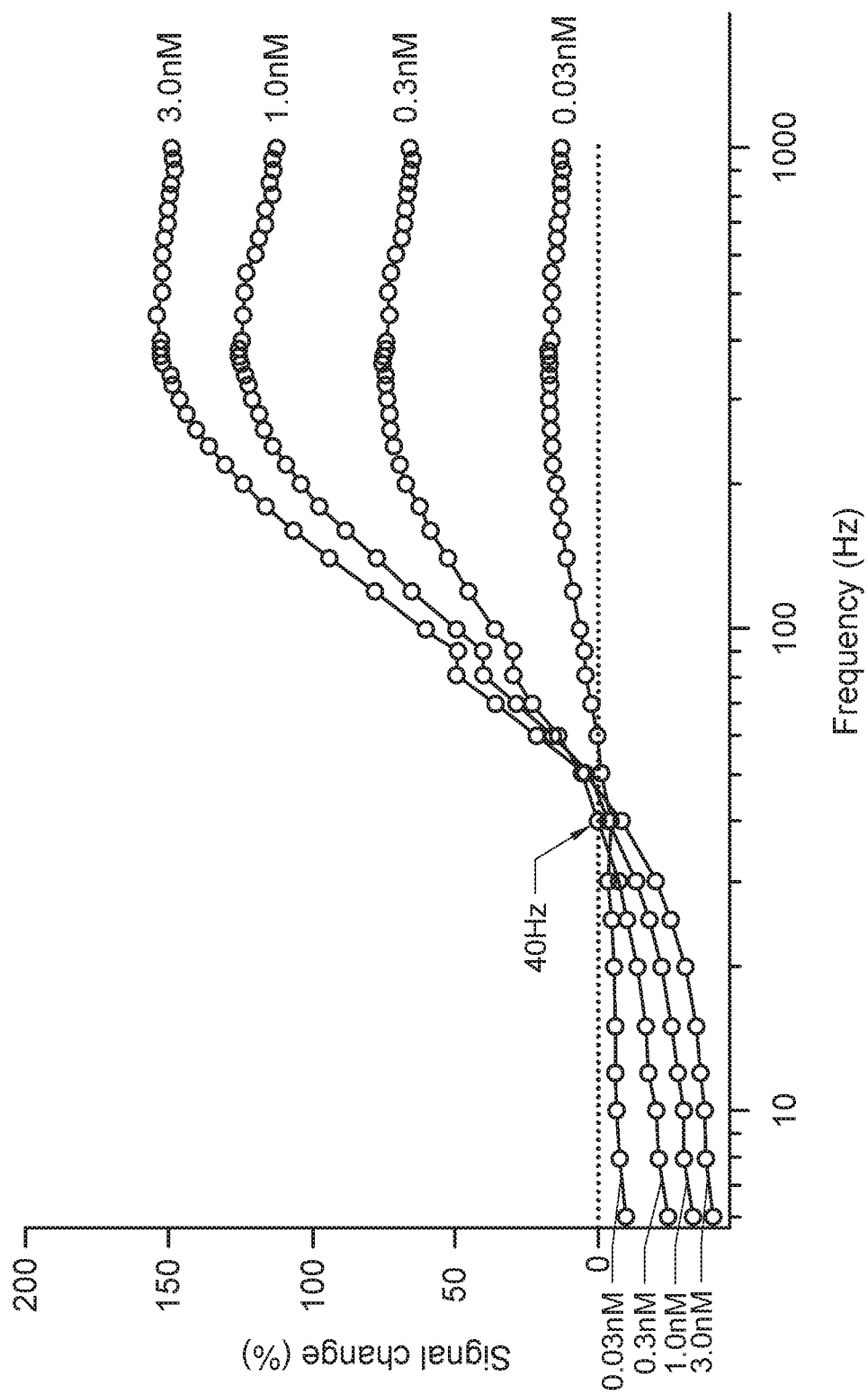
FIGS. 5A and 5B.
Figure 5B:
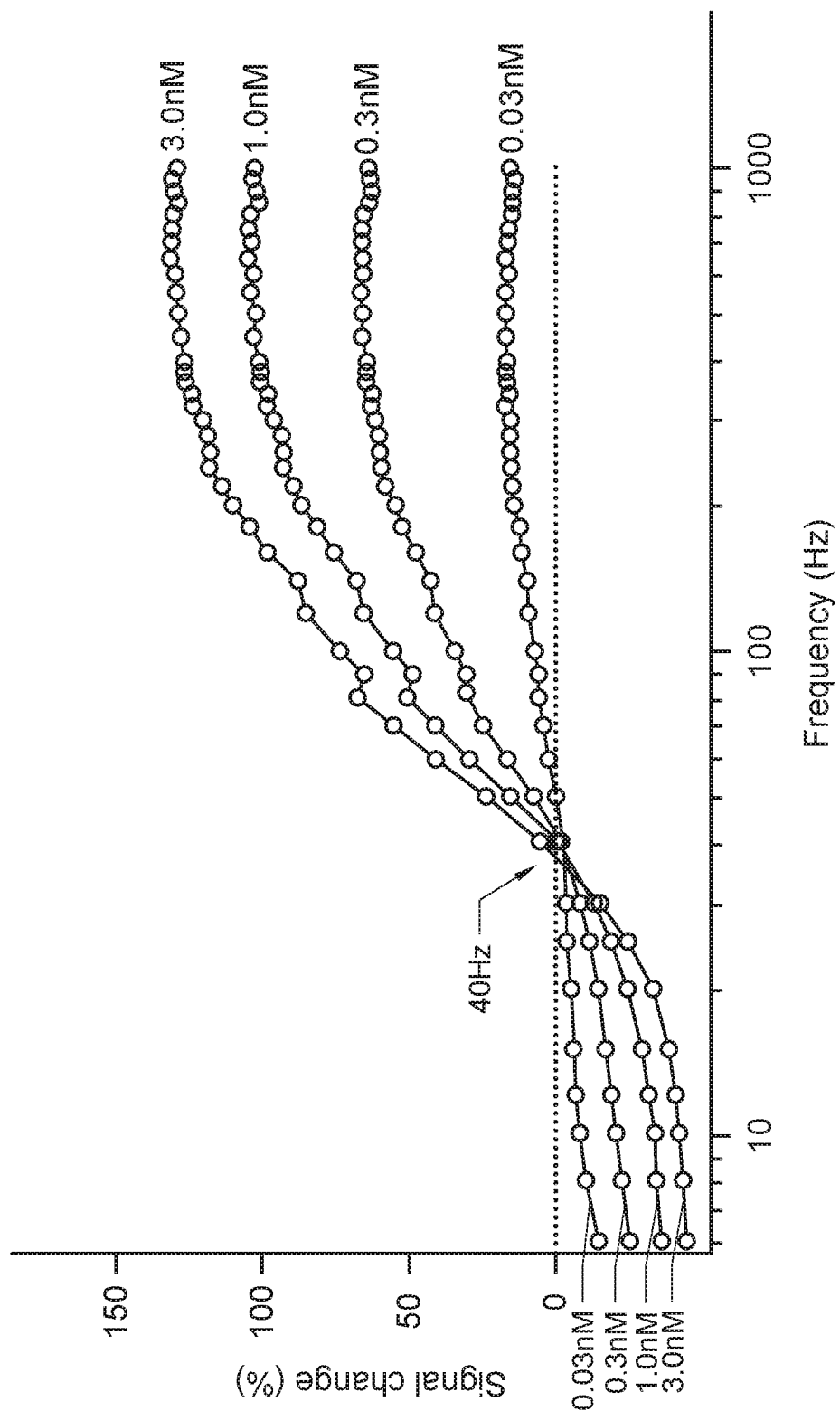
Figure 6A:
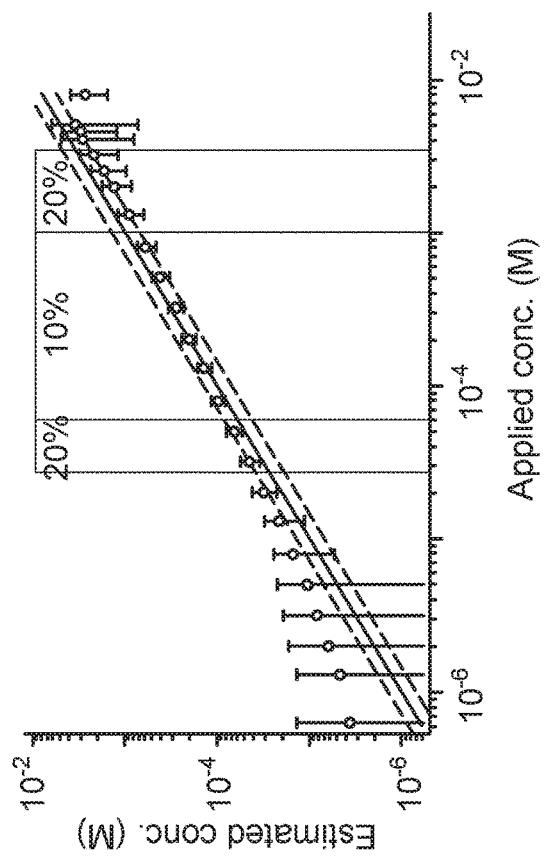
FIGS. 6A and 6B.
Figure 6B:
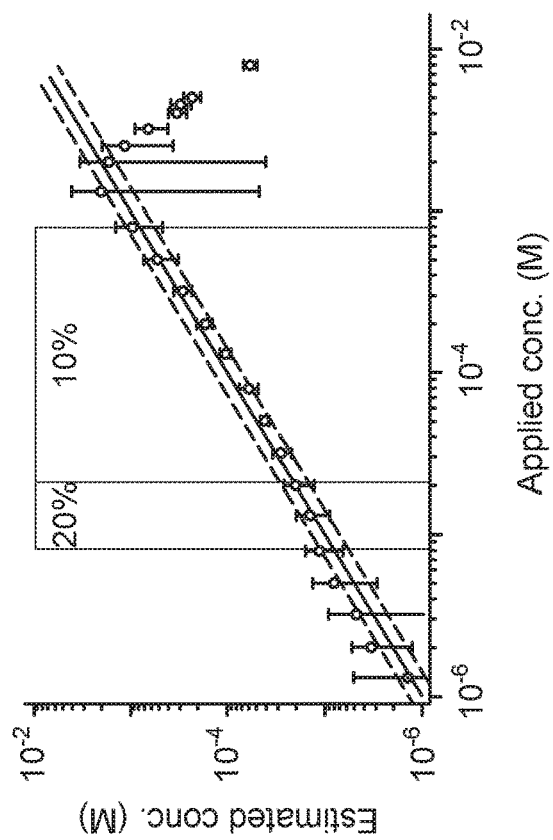

For example, as depicted in FIGS. 5A and 5B, sensor outputs from a training set of six handmade sensors comprising a cocaine-binding aptamer recognition elements was titrated against a range of target concentrations, in both undiluted whole blood and undiluted serum, at a series of frequencies from 1 to 1000 Hz. The nonresponsive frequency, 40 Hz is readily observable as the frequency at which signal change is substantially zero. Global fitting of the training set output was performed to calculate parameters $K_d$, $\alpha$, and $\gamma$. Calculated target concentrations against actual target concentration is depicted in FIGS. 6A and 6B, where it is seen that three independently hand-fabricated sensors interrogated in whole blood are accurate to within 10% of the spiked concentration over the range of 60 µM to 1 mM and within 20% over the range of 20 µM to 2 mM.

It will be understood that modifications and variations of the foregoing method may be utilized in the practice of the invention. Equivalent steps, and/or steps performed in a different order may be utilized and will be within the scope of the invention.

Furthermore, it will be understood that the foregoing illustrations of the general method utilize a responsive frequency that is higher than that of the non-responsive frequency, and which are implemented in a signal-on type sensor. The methods of the invention further extend to the use of responsive frequencies lower than that of the normalizing non-responsive frequency, wherein, in the case of a signal-on type sensor, output will behave inversely, with the relative signal change being negative in response to target binding. The methods may likewise be utilized in signal-off sensor configurations wherein target species binding decreases the output signal.

Multi-Phase Binding.

The foregoing model is premised upon the use of a detection system having recognition elements that bind in a two-state manner (e.g., the recognition element only populates unbound and singly bound states), and for which there exists a square-wave frequency or time point at which the output signals of these two states are identical (the exponential decay curves cross, FIG. 3B), thus rendering the output current a constant irrespective of the target concentration. If, in contrast, some third or higher order state (e.g., a state in which more than one copy of the target molecule is bound to each recognition element) were significantly populated, it would unlikely be the case that all the exponential current decays would cross at a single point, reducing the likelihood of there being a non-responsive frequency at which the sensor output is independent of target concentration. However, even for such multi-phase binding interactions between a target species and the recognition element, a normalization frequency can still be determined and utilized for calibration free measurements.

Figure 8A:
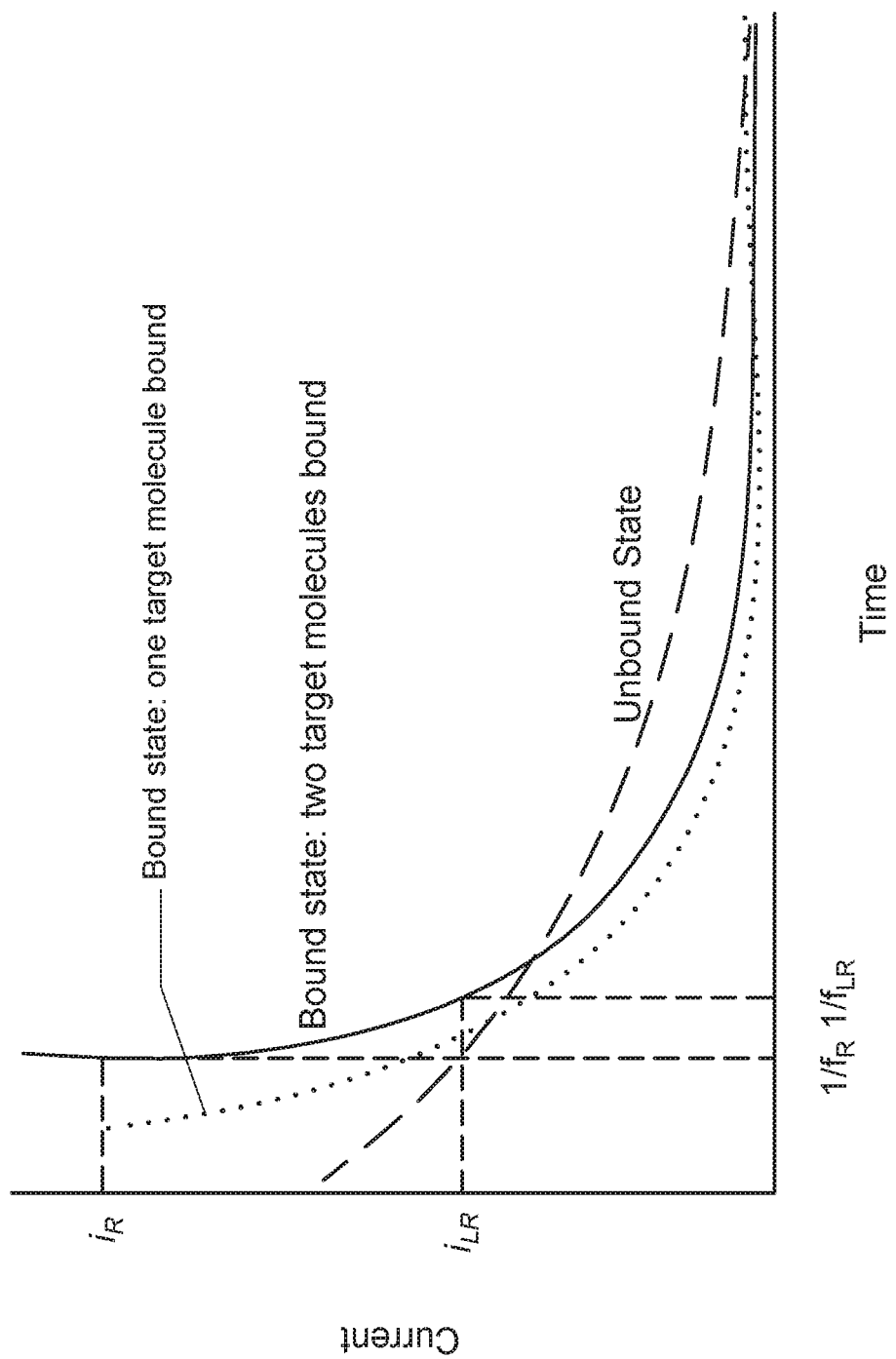
FIG. 8A and FIG. 8B.
Figure 8B:
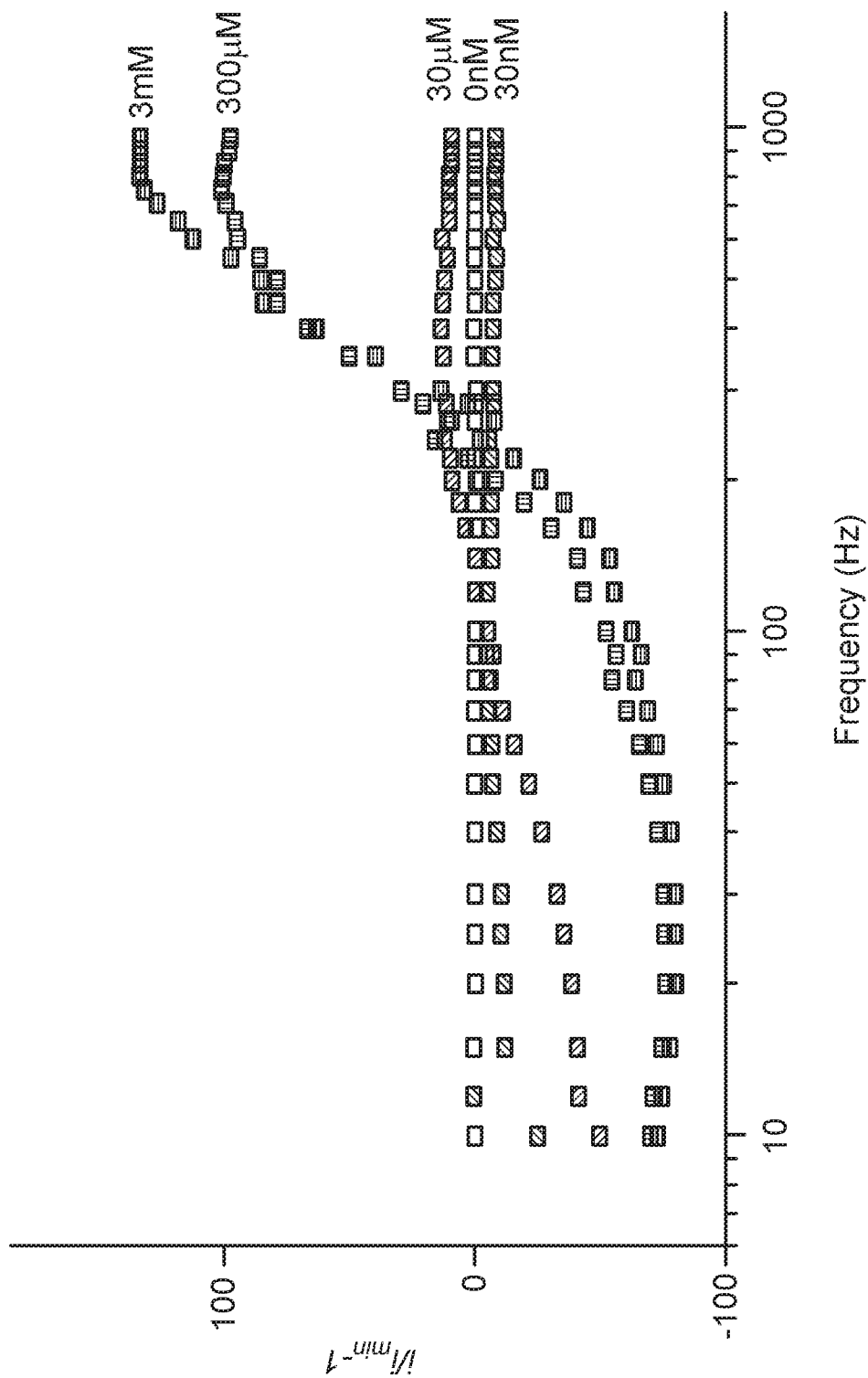

For example, FIG. 8A depicts the excitation decay curves of a sensor employing a kanamycin-binding aptamer, wherein, at higher concentrations, two kanamycin molecules bind. Thus, the current decay kinetics demonstrate multi-phase binding with the aptamer having three binding states: a first with the aptamer being unbound, a second with a single target molecule bound, and a third wherein two target molecules bind. The three states have different current decay kinetics and there is no single point that the three decay curves cross. However, as depicted in FIG. 8B, depicting the frequency response of an E-AB sensor based on the kanamycin binding aptamer, at a frequency of about 250 Hz, the output signal is minimally responsive to target concentration and this value can be used in place of the nonresponsive frequency for estimation of $i_{min}$.

For multi-phase binding systems, using a frequency analysis as above, a "minimally-responsive" frequency, $f_M$, being the frequency at which the sensor responds minimally to target concentration, may be determined, and this minimally responsive frequency can be used as the normalization frequency in place of the non-responsive frequency ($f_{NR}$). In this implementation:

$\alpha_M$ is defined as $i_{min}/i_M^0$, where $i_M^0$, is the current output at the minimally-responsive frequency in the absence of target;

$K_{DM}$ is the mid-point of the $i/i_M$ versus target concentration curve; and $\gamma$ is the ratio of target-saturated output signal to target-free output signal.

Thus, the measurement of target concentration [T] in a sample may be achieved by the following process:

presenting the sample to an electrochemical sensor of a selected design, under a selected set of assay conditions; wherein the electrochemical sensor comprises a plurality of recognition elements bound to an electrode substrate; wherein each recognition element reversibly binds the target species at dissociation constant value $K_{DM}$, wherein the binding of the target to the recognition element may occur in three or more binding states, wherein one or more redox reporter species is associated with each recognition element; and wherein the output of the sensor, upon application of a suitable potential pulse, is a current comprising electron flow between the redox reporter and the electrode substrate;

performing a first interrogation comprising the application of a series of suitable potential pulses to the sensor at a responsive pulse frequency to obtain an output value i, wherein the responsive frequency is a frequency which results in a sensor output that is dependent upon the concentration of the target species in the sample;

performing a second interrogation of the sample comprising the application of a series of suitable potential pulses to the sensor at a minimally responsive pulse frequency to obtain an output value, $i_M^0$, wherein the minimally responsive frequency is a frequency which results in a sensor output that is largely independent of the concentration of the target species in the sample; and calculating the concentration of the target species, [T], by Equation 5:

$$[T] = K_{DM} \frac{i - \alpha\, i_M^0}{\gamma \alpha_M\, i_M^0 - i}$$

wherein $\gamma$ is a constant comprising the ratio of target-saturated output signal to target-free output signal for sensors of the selected design operated under the selected assay conditions;

wherein $K_{DM}$ is the mid-point of the $i/i_M$ versus target concentration curve;

wherein $\alpha_M$ is a constant comprising the ratio of $i_M$ output signal to target-free output signal for sensors of the selected design operated under the selected assay conditions.

Applications of the Invention.

The scope of the invention encompasses methods of measuring target analyte concentration in any number of systems. In one embodiment, the sensors of the invention comprise point-of-care diagnostic tools, wherein a sample withdrawn from the body of a subject (e.g., a human) is analyzed for determining target species concentration. In one embodiment, the point-of-care system comprises a disposable assembly comprising a sensor component (electrode functionalized with recognition elements, reference electrode, reaction chamber) and connectors enabling connection to an external potentiostat/data logger for input of potential pulses at the measurement and nonresponsive frequencies and measurement and recording of output of currents. In one embodiment, the potenentiostat/data logger comprises a mobile device. In one embodiment, the sample comprises an undiluted, unprocessed sample. In one embodiment, the sample comprises a blood drop for example, extracted by a finger stick or like method.

In one embodiment, the invention comprises a method of real-time monitoring by use of a device that is configured to be implanted and/or which is implanted the body of the subject, for example, implanted in the circulatory system, implanted subcutaneously, or implanted within an organ or tissue. The sensor and associated components may be in connection with the ex-vivo environment by trans-cutaneous elements (e.g., catheter or leads) or by wireless communication elements, as known in the art. In one embodiment, the implanted system is utilized for continuous, real-time quantitative measurement of target species in vivo. In one embodiment, the electrochemical sensor is used in a feedback controlled dosing system, wherein the target species is a drug or drug-dependent metabolite, and the measured concentration of the drug or metabolite is used to determine dosing, for example automated dosing by implanted devices. In vivo systems may be used in combination with drift correction methodologies or materials, such as microdialysis membranes, and buffer diffusion layers and other means of preventing with fouling of electrode surfaces.

In one embodiment, the implanted system is used for the measurement of qualitative changes in target species abundance. For example, in one embodiment, the sensor is configured to detect target species concentration exceeding a selected threshold. In other embodiments, the sensors are configured to detect rapid changes in analyte concentration. For example, the detection of a massive upregulation of proinflammatory cytokines in response to an immune event (a "cytokine storm") can cause harmful and even fatal inflammation. An acute myocardial infarction is often accompanied by a large increase in plasma levels of the cardiac troponins; elevation of circulating cardiac troponin above the 99$^{th}$ percentile is sufficient for diagnosis of acute myocardial infarction. These and other diagnostic proteins may be monitored for rapid increases indicative of adverse medical conditions by implanted systems of the invention.

Pre-Calibrated Sensors.

The scope of the invention further encompasses a device, referred to herein as a "pre-calibrated sensor," that can be used in calibration-free measurement of a target species. The pre-calibrated sensor will be a sensor belonging to a class of sensors comprising a common design type, configured to detect a selected target species, wherein a non-responsive frequency and the values of $K_D$, $\alpha$, and $\gamma$ are known for sensors of the same class when operated under a selected set of assay conditions. Because the non-responsive frequency and constants $K_D$, $\alpha$, and $\gamma$ are known for sensors of the class, each individual sensor within the class may be used to measure the concentration of the target species by the calibration-free measurement methods of the invention described above.

In one implementation, the pre-calibrated sensor comprises:
 a sensor for the detection of a target species in a sample, wherein
 the sensor comprises a selected sensor design;
 wherein the sensor comprises a plurality of recognition elements bound to an electrode substrate;
 wherein each recognition element reversibly binds the target species;
 wherein one or more redox reporter species is associated with each recognition element;
 wherein the output of the sensor, upon application of a suitable potential pulse, is a current comprising electron flow between the redox reporter and the electrode substrate;
 wherein a nonresponsive pulse frequency $f_{NR}$ is known for sensors of the class when operated under a selected set of assay conditions;
 wherein the value of the binding dissociation constant $K_D$ of the selected recognition element for the target species is known for sensors of the selected class when operated under the selected set of assay conditions;
 wherein the value of $\gamma$, the constant relating the ratio of target-saturated output signal to target-free output signal is known for sensors of the selected design operated under the selected assay conditions;
 wherein the value of $\alpha$, the constant relating the ratio of $i_{NR}$ output signal to target-free output signal, is known for sensors of the selected design when operated under the selected set of assay conditions.

In one embodiment, the pre-calibrated sensor is a sensor comprising a recognition element wherein the recognition element binds target in a multi-state manner. In such implementation, the pre-calibrated sensor is:
 a sensor for the detection of a target species in a sample, wherein
 the sensor comprises a selected sensor design;
 wherein the sensor comprises a plurality of recognition elements bound to an electrode substrate;
 wherein each recognition element reversibly binds the target species;
 wherein one or more redox reporter species is associated with each recognition element;
 wherein the output of the sensor, upon application of a suitable potential pulse, is a current comprising electron flow between the redox reporter and the electrode substrate;
 wherein a minimally responsive pulse frequency $f_M$ is known for sensors of the class when operated under a selected set of assay conditions;
 wherein $K_{DM}$, the mid-point of the $i/i_M$ versus target concentration curve of the selected recognition element for the target species is known for sensors of the selected class when operated under the selected set of assay conditions;
 wherein the value of $\gamma$, the constant relating the ratio of target-saturated output signal to target-free output signal is known for sensors of the selected design operated under the selected assay conditions;
 wherein the value of am, $i_{min}^0/i_M^0$, where $i_M^0$, is the current output at the minimally-responsive frequency in the absence of target, is known for sensors of the selected design when operated under the selected set of assay conditions.

Pre-calibrated sensors may be used to measure target species concentration in samples without the use of a calibration step. In one embodiment, the pre-calibrated sensor is or is integral to a point of care device. In one embodiment, the pre-calibrated sensor is configured to be implanted in the body of a living animal (e.g., a human subject), for example, comprising a miniaturized sensor designed for in-vivo operation and configured to be in connection with ex-vivo elements. For example, in one embodiment, the in vivo sensor comprises a fully implantable sensor comprising miniaturized elements and wireless, transdermal communication means to transmit data to ex vivo data collection devices. In one embodiment, the in vivo sensor comprises an implantable sensor element with a catheter or like element connecting the ex-vivo power supply, excitation source, and data collection device to the implantable portion. In one embodiment, the in vivo device comprises a needle electrode or is an element integral to an implantable needle assembly. The scope of the invention further encompasses methods of using such pre-calibrated sensors to determine target concentration in a sample.

Software Products.

The scope of the invention further encompasses software systems for performing the methods of the invention. Such software products may encompass machine-readable instructions stored upon a tangible computer readable medium, which such instructions:

direct potentiostats or other sensor operational hardware to deliver a series of suitable potential pulses at a selected non-responsive frequency and at a selected responsive frequency;

to store the output signals generated by the sensor components in response to the potential pulses; and to apply the operations of Equation 4 or equivalent mathematical operations to calculate target concentration.

The scope of the invention further encompasses potentiostat/data logger hardware elements configured to perform the foregoing operations.

EXAMPLES

Example 1. Calibration-Free Measurement of Small Molecules in Undiluted Whole Blood The detection of multiple drugs was demonstrated across dynamic ranges of up to two orders of magnitude without the need to calibrate each individual sensor by the "dual-frequency" approach to calibration-free E-AB sensing. In one experiment, a cocaine-detecting E-AB sensor was utilized, fabricated as described in Baker et al., An Electronic, Aptamer-Based Small-Molecule Sensor for the Rapid, Label-Free Detection of Cocaine in Adulterated Samples and Biological Fluids, *J. Am. Chem. Soc.* 2006, 128, 3138 and Stojanovic et al. Aptamer-Based Folding Fluorescent Sensor for Cocaine, *J. Am. Chem. Soc.* 2001, 123, 4928. Using square wave voltammetry to interrogate such sensors, a responsive frequency, 500 Hz, and a frequency at which the sensor is non-responsive, 40 Hz were identified. A training set of individually hand-made sensors was then titrated across a range of target concentrations while interrogating them at these two frequencies to generate a data set, as depicted in FIG. 5A and FIG. 5B for serum and blood respectively. Each data set was globally fit to Equation 4 to derive $K_d$, $\alpha$, and $\gamma$. Data analysis was performed using in-house built Matlab Scripts (TM) to simultaneously fit data from all the electrodes in a given training set to Equation 4 in order to obtain the optimized parameters $\alpha$, $\gamma$, and $K_D$. The least square errors in the fittings were propagated by Monte-Carlo analysis (10,000 steps) in order to provide a distribution of the variability in the calculated parameters $\alpha$, $\gamma$, and Kr).

With $K_d$, $\alpha$ and $\gamma$ so determined, Equation 4 was applied to measurements of i and $i_{NR}$ obtained from out-of-training set sensors deployed either in undiluted serum or undiluted whole blood. Under the former conditions, the estimated concentration obtained using this dual-frequency approach are accurate to within ±10% (relative to the concentration spiked into the sample) across a 40-fold concentration range and within ±20% across a 100-fold range (FIG. 6A). Estimated target concentrations in undiluted whole blood are accurate to within ±10% across a 15-fold concentration range and within ±20% across a 100-fold range (FIG. 6B). These results compare quite favorably to the accuracy observed for (calibrated) commercial glucose sensors, which can measure across a 30-fold concentration range (1 to 30 mM) with relative error of ±20%.

The dual-frequency approach was repeated for sensors employing other aptamers for the detection of other target species. A sensor against the cancer chemotherapeutic doxorubicin obtained excellent measurement accuracy by the methods of the invention. Specifically, it was observed that, when making measurements in undiluted serum, the estimated target concentrations are accurate to within ±10% of the spiked concentrations across an approximate 3-fold concentration range and within ±20% across a 20-fold range, with these ranges expanding to a 6-fold and a 25-fold concentration spans, respectively, when the sensors were deployed in undiluted whole blood.

To further test the scope of dual-frequency calibration-free E-AB sensing, both cocaine- and doxorubicin-detecting sensors were challenged in flowing whole blood. Under these very demanding conditions the absolute currents generated by cocaine-detecting sensors vary significantly, not only from one sensor to the next but also for a single sensor the course of a few hours. After correction by the application of Equation 4, however, accurate estimates of the applied cocaine concentration were obtained. Similar results likewise were obtained for doxorubicin-detecting sensors in flowing whole blood, with dual-frequency measurements once again enabling the accurate measurements of the target with good accuracy over several hours.

Example 2

Multistate Binding and Minimally Responsive Frequency. The foregoing examples with cocaine and doxorubicin utilized sensors that exhibit non-responsive frequencies, i.e., sensors employing recognition elements that bind in a two-state manner (unbound and singly bound), and for which there exists a square-wave frequency at which the peak currents of these two states are identical thus rendering the output current a constant irrespective of the target concentration. To demonstrate the applicability of the invention to recognition elements that bind in three or higher order states (FIG. 8A), an aminoglycoside-detecting E-AB sensor was tested. Presumably, due to the presence of additional binding event at high target concentrations, such sensor do not exhibit a non-responsive frequency. To perform the calibration-free operation of this sensor a "minimally-responsive" frequency (a frequency at which the sensor responds rather weakly to target; here 250 Hz, FIG. 8B) was used in place of the non-responsive frequency, wherein measurements at this frequency were used as $i_{NR}$ values in Equation 4. As with the previous experiments, the absolute currents obtained from such sensors varied dramatically from sensor to sensor, while the ratio of the currents seen at a highly responsive frequency (here 750 Hz) and the minimally-responsive frequency was highly reproducible. Adapting Equation 4, target concentration was determined without the need for calibration by Equation 5.

In this implementation, $\alpha_M$ is a constant comprising the ratio of $i_M$ output signal to target-free output signal for sensors of the selected design operated under the selected assay conditions and wherein $K_{DM}$ is the mid-point of the $i/i_M$ versus target concentration curve. Using $\alpha_M$, $\gamma$, and $K_{DM}$ defined via global fitting to data collected from a training set of individually hand-fabricated sensors, and then applied to an out-of-training set of sensors, accuracy within ±10% of the spiked kanamycin concentration was achieved across a 25-fold concentration range and ±20% across a 100-fold concentration range.

Example 3

Calibration Free Detection of a Protein Target in Whole Blood. The methods of the invention were tested for the detection of a clinically relevant protein. The sensors in this Example comprised E-AB sensors wherein the recognition element was an aptamer which selectively binds the BB isoform of human platelet-derived growth factor (PDGF), conjugated to a methylene blue redox reporter, wherein binding of PDGF makes the redox reporter more accessible to the electrode surface. When tested across a range of SWV frequencies, a non responsive frequency of 40 Hz was observed and responsive range of frequencies was identified, wherein 300 Hz was selected as a highly responsive frequency. To determine the appropriate values of α, γ and $K_D$ for this class of E-AB sensors, data derived from a training set of six individual sensors titrated with varying concentrations of PDGF in whole blood at the 40 Hz and 300 Hz was globally fit to Equation 4. A global fit of this training set data produced a $K_D$ of 10.9±6 nM, an α of 3.0±0.1, and a γ of 1.1±0.2 for the PDGF-detecting sensor. Sensors from outside the training set were then used to measure target concentration in unprocessed blood samples spiked with PDGF at different concentrations. The calibration-free measurements of the invention produced estimates of target concentration in strong agreement with the known amount of protein added to each unprocessed blood sample, demonstrating the applicability of the methods of the invention to target species comprising a protein in a complex blood sample.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of measuring a concentration of a target species in a sample by a process:
    presenting the sample to an electrochemical sensor of a selected design, under a selected set of assay conditions; wherein the electrochemical sensor comprises a plurality of recognition elements bound to an electrode substrate; wherein each recognition element reversibly binds the target species; wherein one or more redox reporter species is associated with each recognition element; and wherein an output of the sensor, upon application of a suitable potential pulse, is a current comprising electron flow between the redox reporter species and the electrode substrate;
    wherein a ratio of target-saturated output signal to target-free output signal is known for sensors of the selected design operated under the selected assay conditions;
    wherein a ratio of signal output at a minimally-responsive frequency to target-free output signal is known for sensors of the selected design operated under the selected assay conditions;
    performing a first interrogation comprising the application of a series of potential pulses to the sensor at a responsive pulse frequency to obtain an output value i, wherein the responsive frequency is a frequency which results in a sensor output that is dependent upon the concentration of the target species in the sample;
    performing a second interrogation of the sample comprising the application of a series of potential pulses to the sensor at a minimally responsive pulse frequency to obtain an output value $i_{NR}$; and
    calculating the concentration of the target species by use of: i; $i_{NR}$; the ratio of target-saturated output signal to target-free output signal; and the ratio of signal output at the minimally-responsive frequency to target-free output signal.

2. The method of claim 1, wherein:
    each recognition element reversibly binds the target species at a known equilibrium dissociation constant value;
    the minimally responsive pulse frequency is a frequency which results in a sensor output that is substantially independent of the concentration of the target species in the sample; and
    the concentration of the target species, [T] is calculated by an equation $$[T] = K_D \frac{i - \alpha i_{NR}}{\gamma \alpha i_{NR} - i}$$

wherein i is the measured output value at the responsive pulse frequency;
    wherein $i_{NR}$ is the measured output value at the minimally responsive pulse frequency;
    wherein the dissociation constant value is denoted $K_D$;
    wherein γ is a constant comprising the ratio of target-saturated output signal to target-free output signal at the responsive pulse frequency for sensors of the selected design operated under the selected assay conditions; and
    wherein α is a constant comprising the ratio of $i_{NR}$ output signal at the minimally responsive frequency to target-free output signal at the responsive frequency for sensors of the selected design operated under the selected assay conditions.

3. The method of claim 1, wherein
    the binding of the target to the recognition element may occur in three or more binding states; and
    the concentration of the target species, [T], is calculated by an equation $$[T] = K_{DM} \frac{i - \alpha i_M}{\gamma \alpha_M i_M - i}$$

wherein i is the measured output value at the responsive pulse frequency;
    wherein $i_M$ is the measured output value at the minimally responsive pulse frequency;
    wherein γ is a constant comprising the ratio of target-saturated output signal to target-free output signal at the responsive frequency for sensors of the selected design operated under the selected assay conditions;
    wherein $K_{DM}$ is utilized as a dissociation constant and represents a mid-point of an $ili_M$ versus target concentration curve for sensors of the selected design operated under the selected assay conditions; and
    wherein $\alpha_M$ is a constant comprising the ratio of $i_M$ output signal to target-free output signal at the responsive frequency for sensors of the selected design operated under the selected assay conditions.

4. The method of claim 1, wherein
the target species is selected from the group consisting of a small molecule drug, a metabolite, a hormone, a peptide, a protein, a carbohydrate, a nucleic acid sequence, and a pathogen.

5. The method of claim 1, wherein
the sample is selected from the group consisting of blood, serum, plasma, interstitial fluid, urine, a cellular exudate, a cellular extract, a sample derived from foodstuffs, an industrial aqueous sample, and an environmental sample.

6. The method of claim 1, wherein
the sample is unprocessed prior to analysis.

7. The method of claim 1, wherein
the recognition element is an aptamer.

8. The method of claim 1, wherein
the recognition element is a target-binding polypeptide.

9. The method of claim 1, wherein
the series of potential pulses at a selected frequency comprises a squarewave voltammetry sweep.

10. The method of claim 1, wherein
the measurement comprises a point of care measurement.

11. The method of claim 1, wherein
the measurement is an in vivo measurement.

* * * * *